United States Patent
Fukuoka et al.

(10) Patent No.: US 10,365,257 B2
(45) Date of Patent: Jul. 30, 2019

(54) BATTERY INCLUDING GAS DETECTOR FOR DETECTING GAS IN VOID BETWEEN SEAL AND POWER GENERATOR

(71) Applicant: Panasonic Intellectual Property Management Co., Ltd., Osaka (JP)

(72) Inventors: Ayumu Fukuoka, Osaka (JP); Kazuyoshi Honda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 47 days.

(21) Appl. No.: 15/636,743

(22) Filed: Jun. 29, 2017

(65) Prior Publication Data

US 2018/0024102 A1 Jan. 25, 2018

(30) Foreign Application Priority Data

Jul. 19, 2016 (JP) .................. 2016-141437

(51) Int. Cl.
*G01N 31/22* (2006.01)
*H01M 10/42* (2006.01)
*H01M 10/48* (2006.01)

(52) U.S. Cl.
CPC ...... *G01N 31/224* (2013.01); *H01M 10/4228* (2013.01); *H01M 10/48* (2013.01)

(58) Field of Classification Search
CPC . H01M 10/4228; H01M 10/48; G01N 31/224

USPC .............................................. 429/57, 58, 59
See application file for complete search history.

(56) References Cited

U.S. PATENT DOCUMENTS

| | | | | |
|---|---|---|---|---|
| 2003/0072998 | A1* | 4/2003 | Fredriksson | ........ H01M 2/0207 429/210 |
| 2005/0260493 | A1* | 11/2005 | Frederiksson | .......... H01M 2/12 429/210 |
| 2010/0297479 | A1 | 11/2010 | Tsuchida et al. | |
| 2012/0015220 | A1* | 1/2012 | Kawaoka | ............ H01M 10/052 429/90 |
| 2014/0370338 | A1* | 12/2014 | Linn | ..................... H01M 2/348 429/62 |
| 2017/0309968 | A1* | 10/2017 | Komori | ............ H01M 10/4285 |
| 2017/0309975 | A1* | 10/2017 | Iwamoto | ............... H01M 10/52 |

FOREIGN PATENT DOCUMENTS

JP 2009-193727 8/2009

* cited by examiner

*Primary Examiner* — Sean P Cullen
(74) *Attorney, Agent, or Firm* — Greenblum & Bernstein, P.L.C.

(57) ABSTRACT

A battery includes a first power generating element including a first electrode layer and a first counter electrode layer, a first current collector that is in contact with the first electrode layer, a second current collector that is in contact with the first counter electrode layer, a first sealing portion that seals a gap between the first current collector and the second current collector, a first void disposed between the first sealing portion and the first power generating element, and a first gas detection unit that detects gas. The first gas detection unit detects "the gas in the first void".

23 Claims, 24 Drawing Sheets

BATTERY INCLUDING GAS DETECTOR FOR DETECTING GAS IN VOID BETWEEN SEAL AND POWER GENERATOR

BACKGROUND

1. Technical Field

The present disclosure relates to a battery.

2. Description of the Related Art

Japanese Patent No. 5459319 discloses a cell containing a material which chemically reacts with hydrogen sulfide to change electrical resistance thereof and a unit for detecting hydrogen sulfide.

SUMMARY

In the related art, it is desirable to increase gas detection sensitivity.

In one general aspect, the techniques disclosed here feature a battery including a first power generating element including a first electrode layer and a first counter electrode layer, a first current collector that is in contact with the first electrode layer, a second current collector that is in contact with the first counter electrode layer, a first sealing portion that seals a gap between the first current collector and the second current collector, a first void disposed between the first sealing portion and the first power generating element, and a first gas detection unit that detects gas. The first gas detection unit detects the gas in the first void.

According to the present disclosure, gas detection sensitivity can be increased.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Embodiments of the present disclosure will be described with reference to the drawings.

First Embodiment

Figure 1:
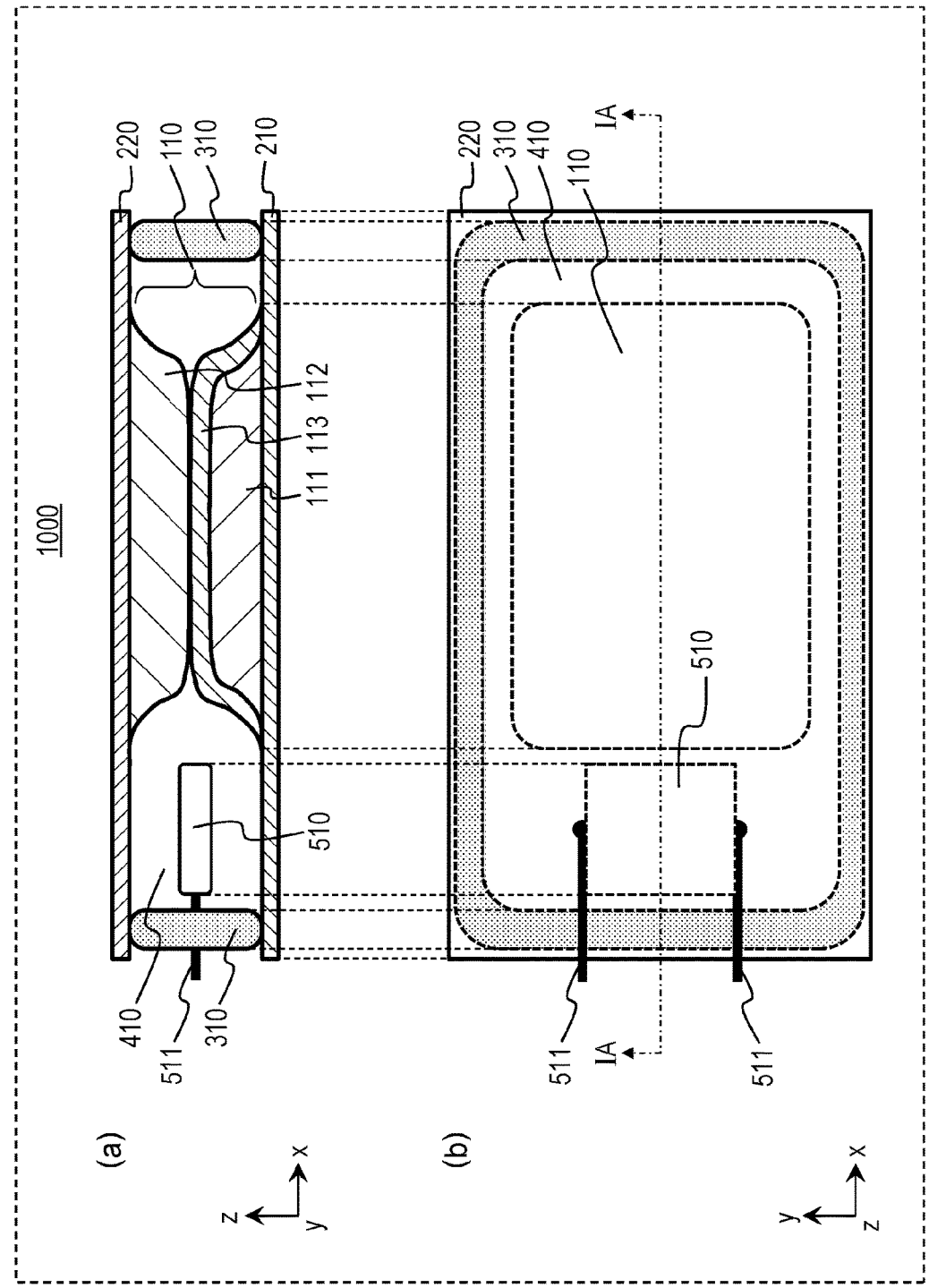
FIG. 1 is a schematic diagram illustrating the structure of a battery according to a first embodiment.

FIG. 1 is a schematic diagram illustrating a battery 1000 according to the first embodiment.

FIG. 1(a) is an x-z view illustrating the structure of the battery 1000 according to the first embodiment (sectional view taken along line IA-IA).

FIG. 1(b) is an x-y view (transparent top view) illustrating the structure of the battery 1000 according to the first embodiment.

The battery 1000 according to the first embodiment includes a first power generating element 110, a first current collector 210, a second current collector 220, a first sealing portion 310, a first void 410, and a first gas detection unit 510.

The first power generating element 110 includes a first electrode layer 111 and a first counter electrode layer 112.

The first current collector 210 is in contact with the first electrode layer 111.

The second current collector 220 is in contact with the first counter electrode layer 112.

The first sealing portion 310 seals the gap between the first current collector 210 and the second current collector 220.

The first void 410 is disposed between the first sealing portion 310 and the first power generating element 110.

The first gas detection unit 510 detects "gas in the first void 410."

According to the above-described structure, gas (for example, hydrogen sulfide gas) can be detected at high detection sensitivity. More specifically, the first sealing portion 310 limits the space accommodating the first power generating element 110, which may generate gas, to the first void 410, which is a small space. Thus, the first void 410, which is a small space, serves as a detection space in which the gas is detected. Accordingly, unlike the case in which the detection space is a larger space in the battery (for example, the space inside an outer cover body), the gas generated by the first power generating element 110 can be prevented from being dissipated and diluted in the larger space. The gas generated by the first power generating element 110 remains in a smaller space, that is, in the first void 410. Therefore, the first gas detection unit 510 can detect the gas in the first void 410 at an early stage while the concentration of the gas is high. As a result, the gas detection sensitivity can be increased.

In addition, according to the above-described structure, the safety of the battery can be increased. More specifically, the region around the first power generating element 110, which may generate gas, is surrounded (for example, sealed) by the first sealing portion 310. When, for example, the battery further includes an outer cover body, the outer cover body and the first sealing portion 310 form a multilayer safety structure. Accordingly, the gas generated by the first power generating element 110 is prevented from being immediately dissipated in the space inside the battery (for example, the space inside the outer cover body) or to the outside of the battery. Therefore, even if the sealed outer cover body is fractured or corroded when the gas is detected, the risk of leakage of harmful gas (for example, hydrogen sulfide gas) to the outside of the battery can be considerably reduced. Thus, the safety of the battery can be increased.

Figure 24:
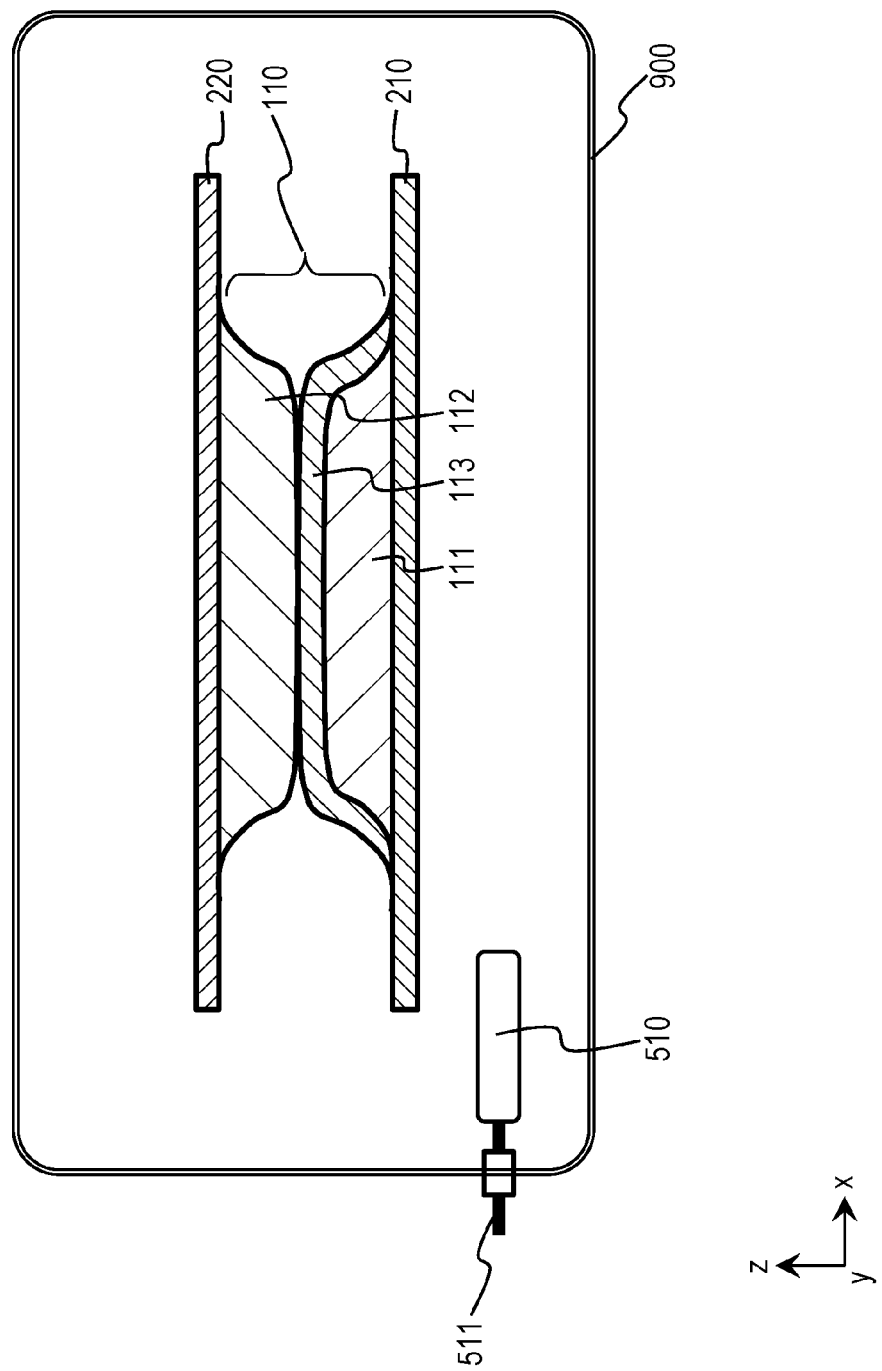
FIG. 24 is a schematic sectional view illustrating the structure of a battery according to a comparative example.

FIG. 24 is a schematic sectional view illustrating the structure of a battery according to a comparative example.

The battery according to the comparative example illustrated in FIG. 24 does not include the first sealing portion 310. Therefore, the battery according to the comparative example does not have the first void 410.

The battery according to the comparative example includes an outer cover body 900. The outer cover body 900 contains a first power generating element 110, a first current collector 210, a second current collector 220, and a first gas detection unit 510.

In the battery according to the comparative example, the first gas detection unit 510 is disposed in the outer cover body 900.

In the battery according to the comparative example, the detection space of the first gas detection unit 510 is a large space in the battery (space inside the outer cover body 900). Therefore, it is difficult to detect the gas at an early stage while the concentration of the gas is high. In addition, since the battery according to the comparative example does not include the first sealing portion 310, there is a high risk that the gas will flow out of the battery if the outer cover body 900 is fractured or corroded when the gas is detected.

In contrast, in the battery 1000 according to the first embodiment, as described above, the first void 410, which is a small space, serves as the detection space in which the gas is detected, so that the gas detection sensitivity can be increased. In addition, since the battery 1000 according to the first embodiment includes the first sealing portion 310, the risk of leakage of harmful gas to the outside of the battery can be considerably reduced.

The first electrode layer 111 contains a first electrode material.

The first counter electrode layer 112 serves as a counter electrode for the first electrode layer 111. The first counter electrode layer 112 contains a first counter electrode material.

In the first power generating element 110, one of the first electrode layer 111 and the first counter electrode layer 112 is a positive electrode layer, and the other is a negative electrode layer.

For example, the first electrode layer 111 may be a positive electrode layer. In this case, the first electrode material is a positive electrode material. The first counter electrode layer 112 is a negative electrode layer. The first counter electrode material is a negative electrode material. The first current collector 210 is a positive electrode current collector. The second current collector 220 is a negative electrode current collector.

The first electrode layer 111 may instead be a negative electrode layer. In this case, the first electrode material is a negative electrode material. The first counter electrode layer 112 is a positive electrode layer. The first counter electrode material is a positive electrode material. The first current collector 210 is a negative electrode current collector. The second current collector 220 is a positive electrode current collector.

The first power generating element 110 according to the first embodiment is, for example, a power generating element having charging and discharging characteristics.

Specific examples of a power generating element and current collectors according to the first embodiment will now be described.

A power generating element according to the first embodiment includes, for example, a positive electrode layer, a negative electrode layer, and a solid electrolyte layer.

The positive electrode layer is, for example, a positive electrode active substance layer. The positive electrode active substance layer is a layer containing a positive electrode active substance, which is a positive electrode material. The positive electrode active substance contained in the positive electrode active substance layer may be a known positive electrode active substance (for example, lithium cobalt oxide or LiNO). Various materials that allow Li to be inserted and extracted may be used as a material of the positive electrode active substance.

The positive electrode layer may be provided as a positive electrode mixture layer composed of a positive electrode active substance layer containing an additional material. A known solid electrolyte (for example, an inorganic solid electrolyte) may be used as the additional material contained in the positive electrode active substance layer. The inorganic solid electrolyte may be, for example, a sulfide solid electrolyte or an oxide solid electrolyte. The sulfide solid electrolyte may be, for example, a mixture of $Li_2S:P_2S_5$. The surface of the positive electrode active substance may be coated with a solid electrolyte. A conductive material (for example, acetylene black), a binder (for example, polyvinylidene fluoride), etc., may also be used as the additional material contained in the positive electrode active substance layer.

The positive electrode layer may be formed by applying a paste-like coating material, prepared by kneading the positive electrode active substance and the additional material together with a solvent, to a surface of the positive electrode current collector and drying the coating material. The positive electrode layer may be pressed after the drying process to increase the density thereof. The thus-formed positive electrode layer has a thickness of, for example, 5 to 300 μm.

The negative electrode layer is, for example, a negative electrode active substance layer. The negative electrode active substance layer is a layer containing a negative electrode active substance, which is a negative electrode material. The negative electrode active substance contained in the negative electrode active substance layer may be a known negative electrode active substance (for example, graphite). Various materials that allow Li to be inserted and extracted may be used as a material of the negative electrode active substance.

The negative electrode layer may be provided as a negative electrode mixture layer composed of a negative electrode active substance layer containing an additional material. A known solid electrolyte (for example, an inorganic solid electrolyte) may be used as the additional material contained in the negative electrode active substance layer. The inorganic solid electrolyte may be, for example, a sulfide solid electrolyte or an oxide solid electrolyte. The sulfide solid electrolyte may be, for example, a mixture of $Li_2S:P_2S_5$. A conductive material (for example, acetylene black), a binder (for example, polyvinylidene fluoride), etc., may also be used as the additional material contained in the negative electrode active substance layer.

The negative electrode layer may be formed by applying a paste-like coating material, prepared by kneading the negative electrode active substance and the additional material together with a solvent, to a surface of the negative electrode current collector and drying the coating material. The negative electrode layer may be pressed after the drying process to increase the density thereof. The thus-formed negative electrode layer has a thickness of, for example, 5 to 300 μm.

In the power generating element, the area in which the negative electrode active substance layer is formed may be greater than the area in which the positive electrode active substance layer is formed. In this case, it may be possible to prevent malfunctioning of the battery (for example, reduction in reliability) due to, for example, lithium precipitation.

Alternatively, in the power generating element, the area in which the positive electrode active substance layer is formed may be the same as the area in which the negative electrode active substance layer is formed.

The solid electrolyte layer is a layer containing a solid electrolyte. The solid electrolyte layer is disposed between, for example, the positive electrode layer and the negative electrode layer.

A known solid electrolyte (for example, an inorganic solid electrolyte) may be used as the solid electrolyte contained in the solid electrolyte layer. The inorganic solid electrolyte may be, for example, a sulfide solid electrolyte or an oxide solid electrolyte. The sulfide solid electrolyte may be, for example, a mixture of $Li_2S:P_2S_5$. The sulfide solid electrolyte has high ionic conductivity and flexibility.

A binder (for example, polyvinylidene fluoride) may be used as an additional material contained in the solid electrolyte layer.

The solid electrolyte layer may be formed by applying a paste-like coating material, prepared by kneading the solid electrolyte and the additional material together with a solvent, to the positive electrode active substance layer or the negative electrode active substance layer and drying the coating material. The power generating element may be formed by compressing the multilayer structure including the positive electrode current collector, the positive electrode layer, the solid electrolyte layer, the negative electrode layer, and the negative electrode current collector. As a result of the compressing process, the layers are tightly and appropriately joined together. The layers may be joined together so that the area in which the positive electrode layer is formed does not protrude from the area in which the negative electrode layer, facing the positive electrode layer, is formed.

In the power generating element, the positive electrode layer and the negative electrode layer may be formed in an area smaller than the area in which the positive electrode current collector and the negative electrode current collector are formed. The solid electrolyte layer may have an area larger than the area of the positive electrode active substance layer and the negative electrode active substance layer. Accordingly, a short circuit due to direct contact between the positive electrode layer and the negative electrode layer can be prevented.

In addition, in the power generating element, the solid electrolyte layer may be formed in the same area as the area in which the positive electrode current collector or the negative electrode current collector is formed.

Alternatively, in the power generating element, the solid electrolyte layer may be formed in an area smaller than the area in which the positive electrode current collector or the negative electrode current collector is formed.

The positive electrode current collector may be composed of, for example, a metal foil (for example, a SUS foil or an Al foil). The positive electrode current collector may have a thickness of, for example, 5 to 100 μm.

The negative electrode current collector may be composed of, for example, a metal foil (for example, a SUS foil or a Cu foil). The negative electrode current collector may have a thickness of, for example, 5 to 100 μm.

There is no particular limitation regarding the order in which the layers of the power generating element are formed. The method for forming the layers of the power generating element may be, for example, successive stacking, bonding, transferring, or a combination thereof.

In the battery 1000 according to the first embodiment, as illustrated in FIG. 1, the first power generating element 110 may include a first solid electrolyte layer 113.

The first solid electrolyte layer 113 is disposed between the first electrode layer 111 and the first counter electrode layer 112.

At least one of the first electrode layer 111, the first counter electrode layer 112, and the first solid electrolyte layer 113 may contain a first sulfur-based material.

The gas may contain hydrogen sulfide gas generated due to the first sulfur-based material.

The first gas detection unit 510 may detect "the hydrogen sulfide gas in the first void 410."

According to the above-described structure, a laminate battery (all-solid lithium secondary battery) including a solid electrolyte can be realized, and the hydrogen sulfide gas detection sensitivity can be increased.

The first solid electrolyte layer 113 is a layer containing a first solid electrolyte. The first solid electrolyte may be, for example, the above-described solid electrolyte.

The first sulfur-based material may be, for example, the above-described sulfide solid electrolyte.

The first sulfur-based material is, for example, a material that generates hydrogen sulfide ($H_2S$) gas by reacting with water.

The first sealing portion 310 may be made of a commonly known sealing material (for example, a thermoplastic resin, a thermosetting resin, or a photo-curing resin). The material of the first sealing portion 310 may have a high ability to prevent permeation of, for example, water, enclosed gas, or gas that may be generated by the first power generating element 110. The first sealing portion 310 prevents entrance of water, thereby preventing, for example, corrosion and deterioration of the current collectors, degeneration of the solid electrolyte, and generation of toxic gas.

As illustrated in FIG. 1, the first sealing portion 310 may seal the periphery (for example, four sides) of the first power generating element 110.

The first void 410 is at least a void (space) disposed between the first sealing portion 310 and the first power generating element 110.

The expression "the first void 410 is disposed between the first sealing portion 310 and the first power generating element 110" includes the case in which "the first void 410 is disposed between (surrounded by) the first sealing portion 310, the first power generating element 110, and other components".

For example, as illustrated in FIG. 1, the first void 410 may be a void (space) surrounded by the first sealing portion 310, the first power generating element 110, the first current collector 210, and the second current collector 220.

Alternatively, when the surface of the first current collector 210 is covered by a component of the first power generating element 110 (the first electrode layer 111 or the first solid electrolyte layer 113), the first void 410 may be a void (space) surrounded by the first sealing portion 310, the first power generating element 110, and the second current collector 220.

Alternatively, when the surface of the second current collector 220 is covered by a component of the first power generating element 110 (the first counter electrode layer 112 or the first solid electrolyte layer 113), the first void 410 may be a void (space) surrounded by the first sealing portion 310, the first power generating element 110, and the first current collector 210.

Alternatively, when the surfaces of the first current collector 210 and the second current collector 220 are covered by components of the first power generating element 110, the first void 410 may be a void (space) surrounded only by the first sealing portion 310 and the first power generating element 110.

Alternatively, when the surface of the first current collector 210 is covered by the first sealing portion 310, the first void 410 may be a void (space) surrounded by the first sealing portion 310, the first power generating element 110, and the second current collector 220.

Alternatively, when the surface of the second current collector 220 is covered by the first sealing portion 310, the first void 410 may be a void (space) surrounded by the first sealing portion 310, the first power generating element 110, and the first current collector 210.

Alternatively, when the surfaces of the first current collector 210 and the second current collector 220 are covered by the first sealing portion 310, the first void 410 may be a void (space) surrounded only by the first sealing portion 310 and the first power generating element 110.

As illustrated in FIG. 1, the first void 410 may be formed at the periphery (for example, four sides) of the first power generating element 110.

The first gas detection unit 510 is a member that detects gas generated by the first power generating element 110. The first gas detection unit 510 may be a commonly known gas detection sensor (for example, a constant potential electrolysis sensor, a semiconductor sensor, or a heat conduction sensor) or a combination of these sensors.

The first gas detection unit 510 may contain a resistance variable material (for example, a metal material such as copper) that chemically reacts with gas (for example, hydrogen sulfide) to change the electrical resistance thereof.

As illustrated in FIG. 1, the first gas detection unit 510 may be a thin sensor. In such a case, the enclosing structure for the first gas detection unit 510 can be simplified. In addition, the volume of the space occupied by the first gas detection unit 510 can be reduced.

In the battery 1000 according to the first embodiment, as illustrated in FIG. 1, the first gas detection unit 510 may be disposed in the first void 410.

According to the above-described structure, the gas detection sensitivity can be increased. More specifically, the gas generated by the first power generating element 110 and remaining in the first void 410 can be detected in the first void 410. Therefore, the first gas detection unit 510 can detect the gas in the first void 410 at an early stage while the concentration of the gas is high.

In the present disclosure, the expression "the first gas detection unit 510 is disposed in the first void 410" includes the arrangement in which "the entirety of the first gas detection unit 510 is disposed in the first void 410" as illustrated in FIG. 1.

Figure 2:
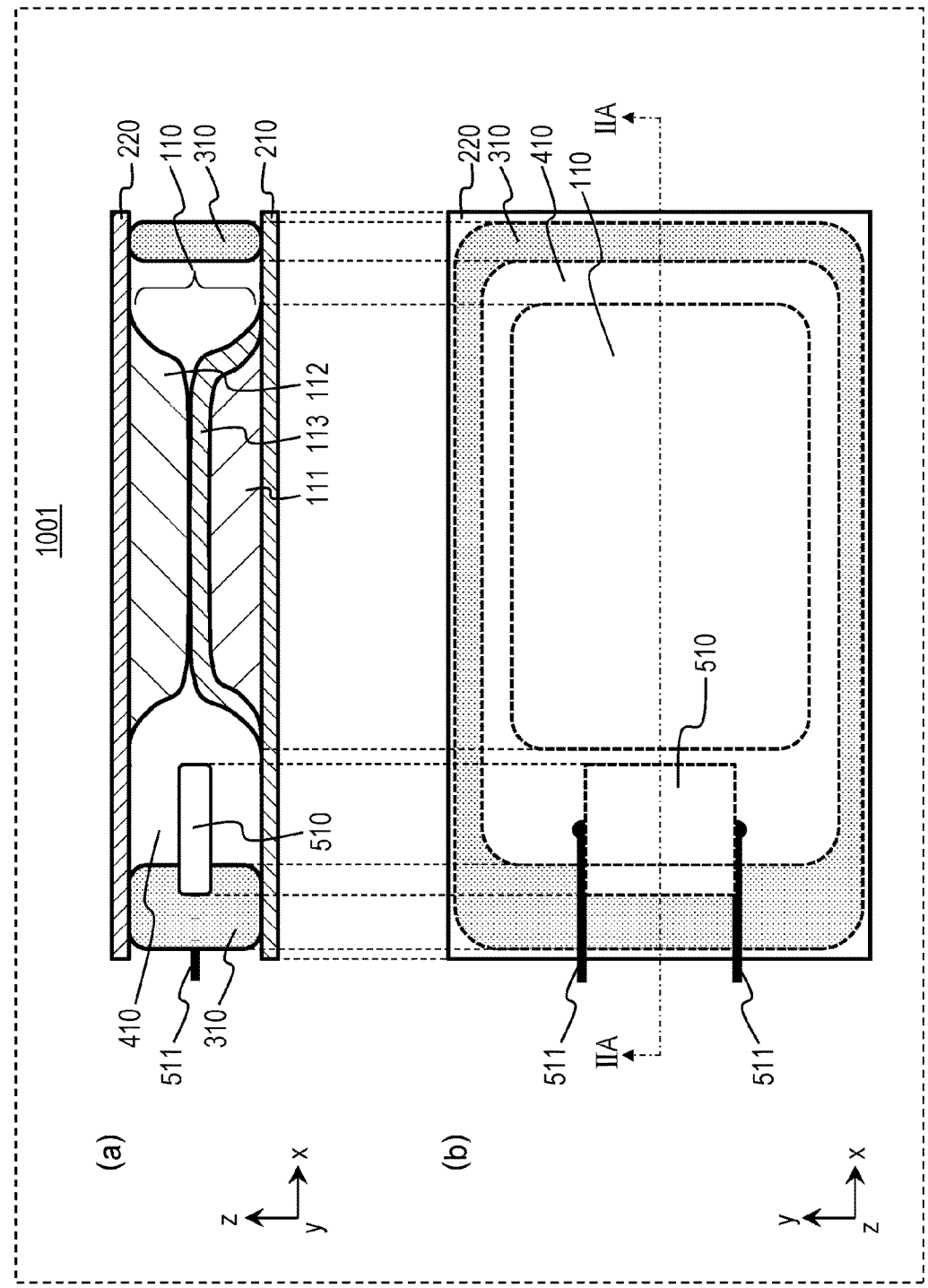
FIG. 2 is a schematic diagram illustrating the structure of a battery according to the first embodiment.
Figure 3:
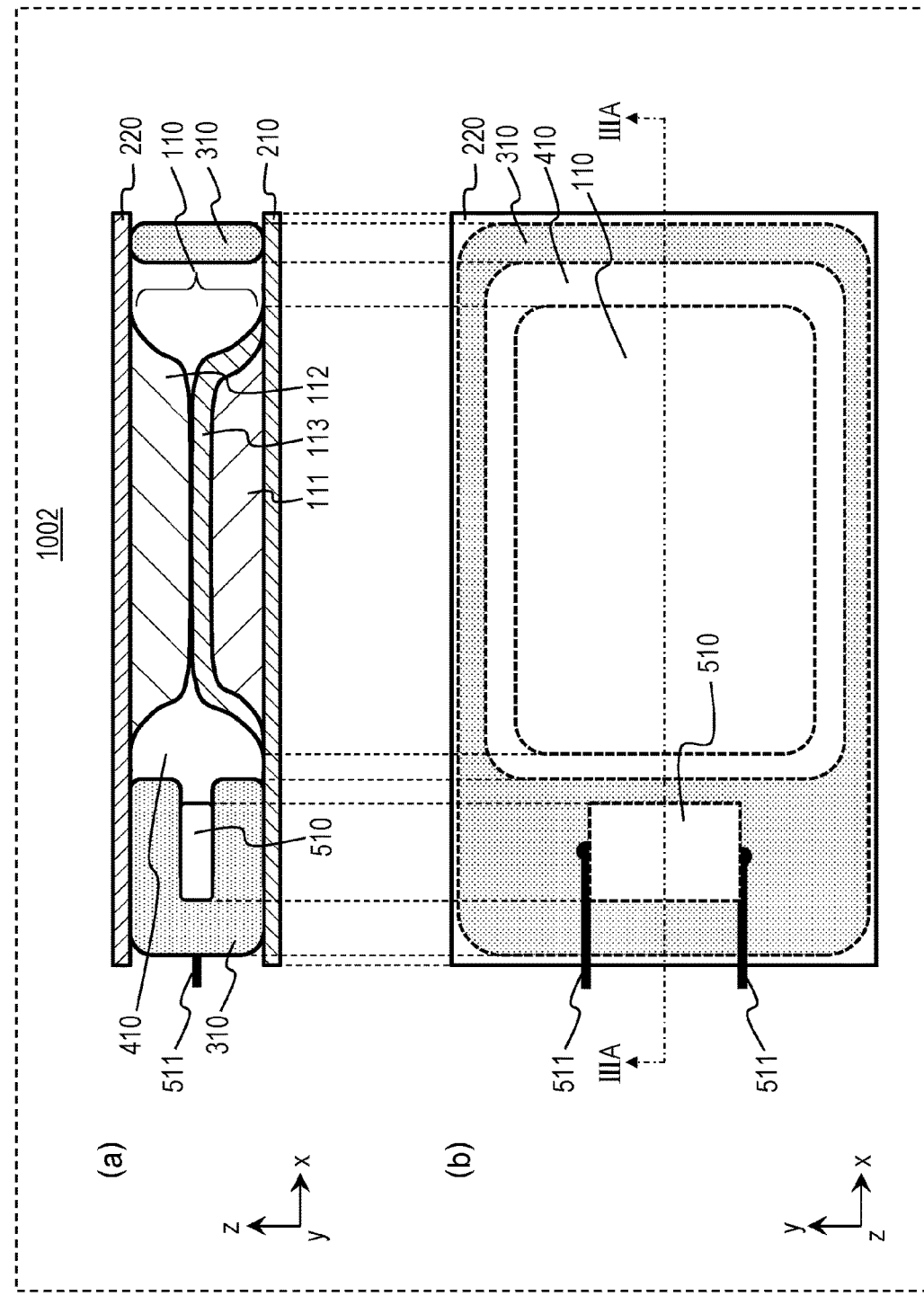
FIG. 3 is a schematic diagram illustrating the structure of a battery according to the first embodiment.
Figure 4:
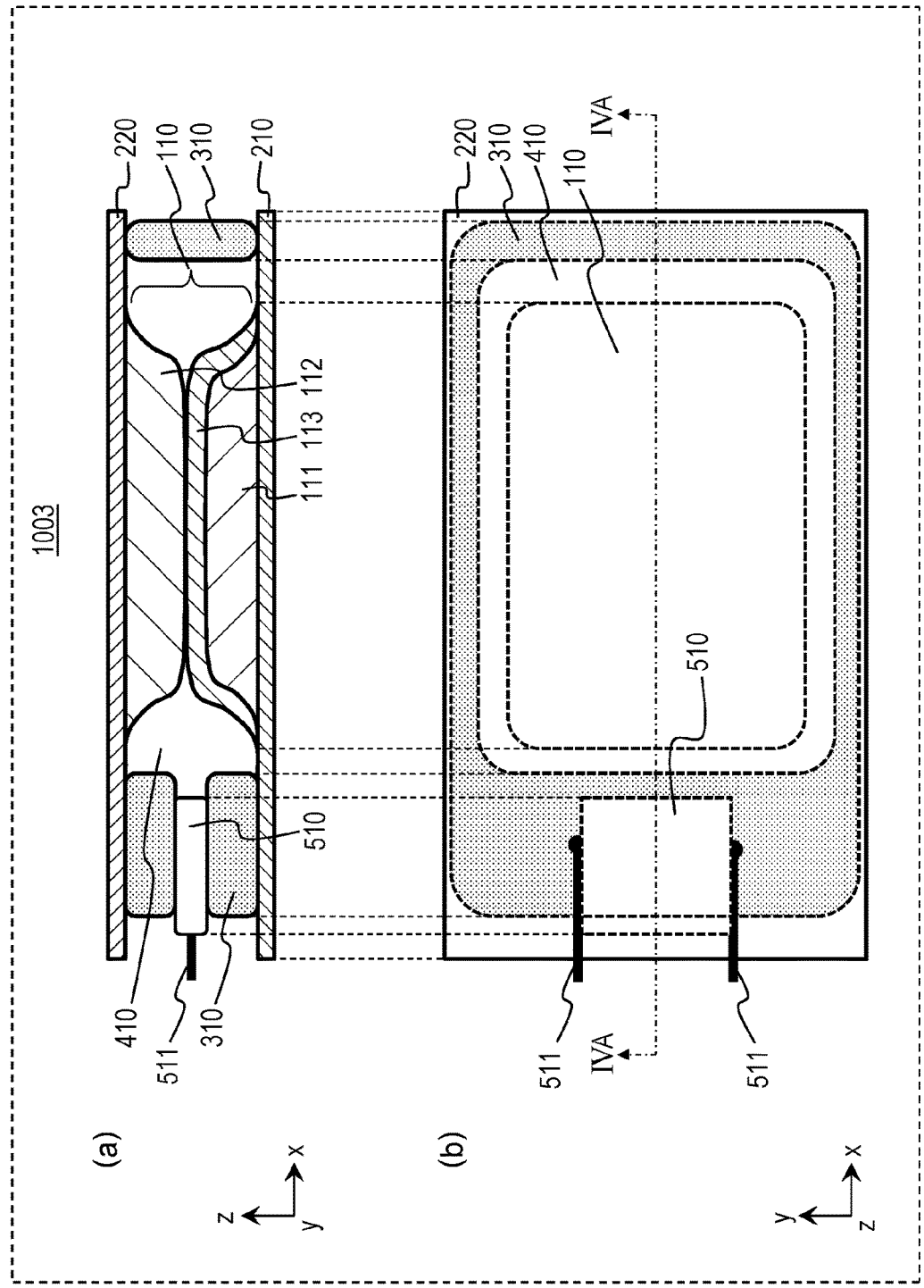
FIG. 4 is a schematic diagram illustrating the structure of a battery according to the first embodiment.

In addition, in the present disclosure, the expression "the first gas detection unit 510 is disposed in the first void 410" also includes the arrangement in which "a portion of the first gas detection unit 510 is disposed in the first void 410" as illustrated in FIGS. 2, 3, and 4.

FIG. 2 is a schematic diagram illustrating a battery 1001 according to the first embodiment.

FIG. 2(*a*) is an x-z view illustrating the structure of the battery 1001 according to the first embodiment (sectional view taken along line IIA-IIA).

FIG. 2(*b*) is an x-y view (transparent top view) illustrating the structure of the battery 1001 according to the first embodiment.

As illustrated in FIG. 2, in the battery 1001 according to the first embodiment, a portion (for example, an end portion) of the first gas detection unit 510 is embedded in the first sealing portion 310. Accordingly, a portion of the first gas detection unit 510 is disposed in the first void 410.

According to this structure, the first sealing portion 310 is allowed to be in contact with a portion of the first gas detection unit 510. Therefore, it is not necessary to precisely position the first sealing portion 310 when the first sealing portion 310 is formed. Thus, the process of forming the first sealing portion 310 can be simplified.

FIG. 3 is a schematic diagram illustrating a battery 1002 according to the first embodiment.

FIG. 3(*a*) is an x-z view illustrating the structure of the battery 1002 according to the first embodiment (sectional view taken along line IIIA-IIIA).

FIG. 3(*b*) is an x-y view (transparent top view) illustrating the structure of the battery 1002 according to the first embodiment.

As illustrated in FIG. 3, in the battery 1002 according to the first embodiment, a portion (for example, a portion other than an end portion) of the first gas detection unit 510 is embedded in the first sealing portion 310. Accordingly, a portion (for example, an end portion) of the first gas detection unit 510 is disposed in the first void 410.

According to this structure, the first sealing portion 310 is allowed to be in contact with the major portion of the first gas detection unit 510. Therefore, it is not necessary to precisely position the first sealing portion 310 when the first sealing portion 310 is formed. Thus, the process of forming the first sealing portion 310 can be simplified.

FIG. 4 is a schematic diagram illustrating a battery 1003 according to the first embodiment.

FIG. 4(a) is an x-z view illustrating the structure of the battery 1003 according to the first embodiment (sectional view taken along line IVA-IVA).

FIG. 4(b) is an x-y view (transparent top view) illustrating the structure of the battery 1003 according to the first embodiment.

As illustrated in FIG. 4, in the battery 1003 according to the first embodiment, a portion (for example, portions of principal surfaces) of the first gas detection unit 510 is embedded in the first sealing portion 310. Accordingly, a portion (for example, an end portion) of the first gas detection unit 510 is disposed in the first void 410.

According to this structure, the first sealing portion 310 is allowed to be in contact with the major portion of the first gas detection unit 510. Therefore, it is not necessary to precisely position the first sealing portion 310 when the first sealing portion 310 is formed. Thus, the process of forming the first sealing portion 310 can be simplified.

As illustrated in FIG. 1, the battery 1000 according to the first embodiment may further include two first connection lines 511.

The first gas detection unit 510 may have a sensing region (for example, a portion formed of a resistance variable material) that is connected to one end of each of the two first connection lines 511.

In the battery 1000 according to the first embodiment, the other end of each of the two first connection lines 511 extends to, for example, the outside of the battery 1000 through the first sealing portion 310.

The two first connection lines 511 that extend to the outside of the battery 1000 may be connected to a detection device for detecting gas. In other words, the battery 1000 and the detection device may be configured to form a battery system (detection system).

For example, the detection device may cause a current to flow between the two first connection lines 511 and detect the voltage between the two first connection lines 511. The presence or absence of gas is determined on the basis of the magnitude and variation of the voltage. The detection device may include, for example, a current applying unit (for example, a current source) and a voltage measurement unit (for example, a voltmeter). The current applying unit and the voltage measurement unit may have commonly known structures.

Alternatively, the detection device may apply a voltage between the two first connection lines 511 and detect the current between the two first connection lines 511. The presence or absence of gas is determined on the basis of the magnitude and variation of the current. The detection device may include, for example, a voltage applying unit (for example, a voltage source) and a current measurement unit (for example, a current meter). The voltage applying unit and the current measurement unit may have commonly known structures.

The detection device may further include a control unit. The control unit may control the current applying unit, the voltage measurement unit, the voltage applying unit, and the current measurement unit. The control unit may determine the presence or absence of gas.

The control unit may include, for example, a processor and a memory. The processor may be, for example, a central processing unit (CPU) or a micro-processing unit (MPU). The processor may carry out a control method according to the present disclosure by reading a program stored in the memory and executing the program.

Figure 5:
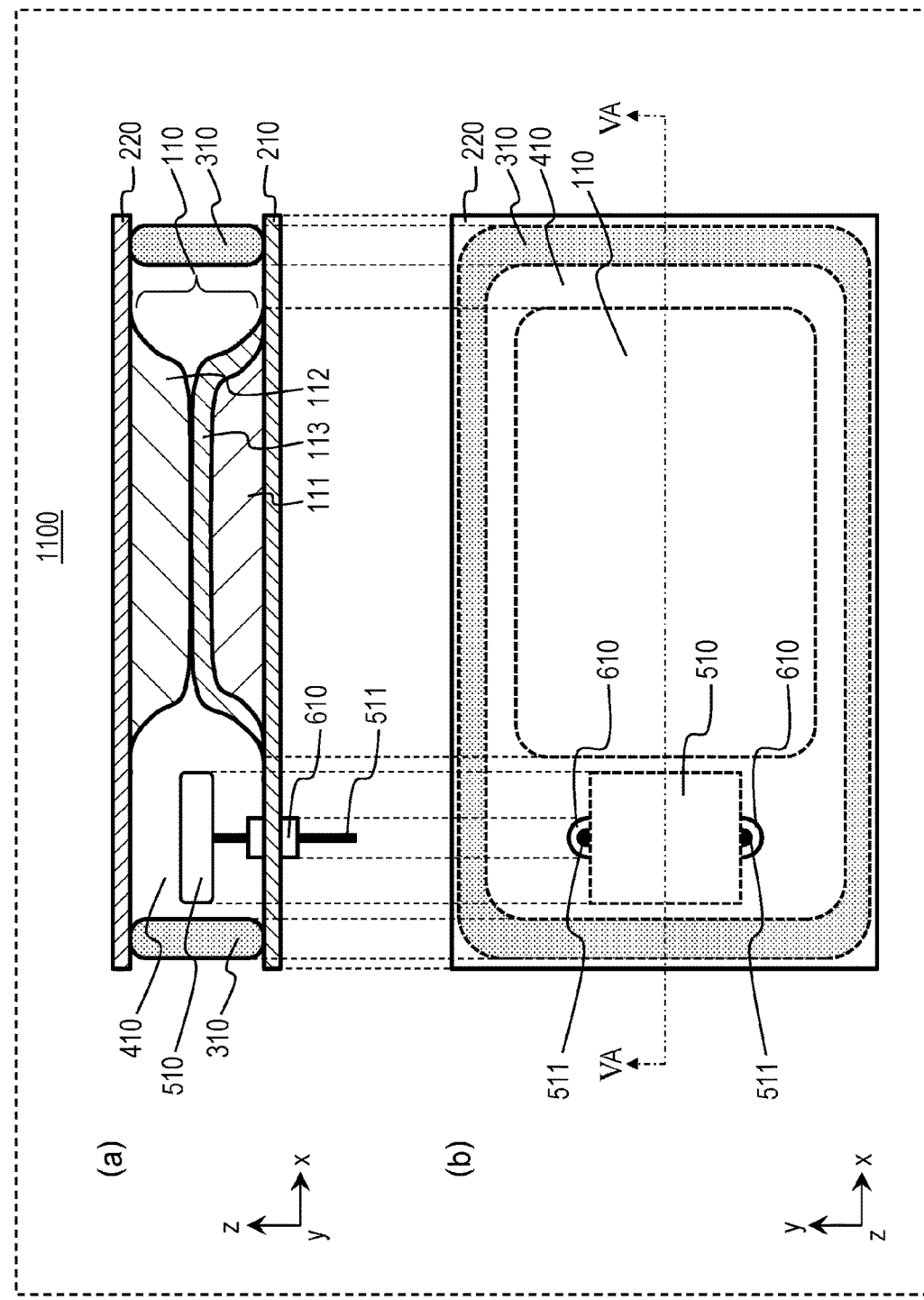
FIG. 5 is a schematic diagram illustrating the structure of a battery according to the first embodiment.

FIG. 5 is a schematic diagram illustrating a battery 1100 according to the first embodiment.

FIG. 5(a) is an x-z view illustrating the structure of the battery 1100 according to the first embodiment (sectional view taken along line VA-VA).

FIG. 5(b) is an x-y view (transparent top view) illustrating the structure of the battery 1100 according to the first embodiment.

In the battery 1100 according to the first embodiment, the first current collector 210 includes first passage portions 610.

The first gas detection unit 510 includes the first connection lines 511.

The first connection lines 511 extend to the outside through the first passage portions 610.

According to the above-described structure, the structure for enabling the first connection lines 511 of the first gas detection unit 510 to extend to the outside can be more easily formed than in the case where the first connection lines 511 extend to the outside through the first sealing portion 310 (as in the above-described battery 1000).

Each first passage portion 610 may include, for example, an opening formed in the first current collector 210 and a sealing portion that seals the gap between the opening and the corresponding first connection line 511. The material of the sealing portion may be the same as the material of the above-described first sealing portion 310.

Figure 6:
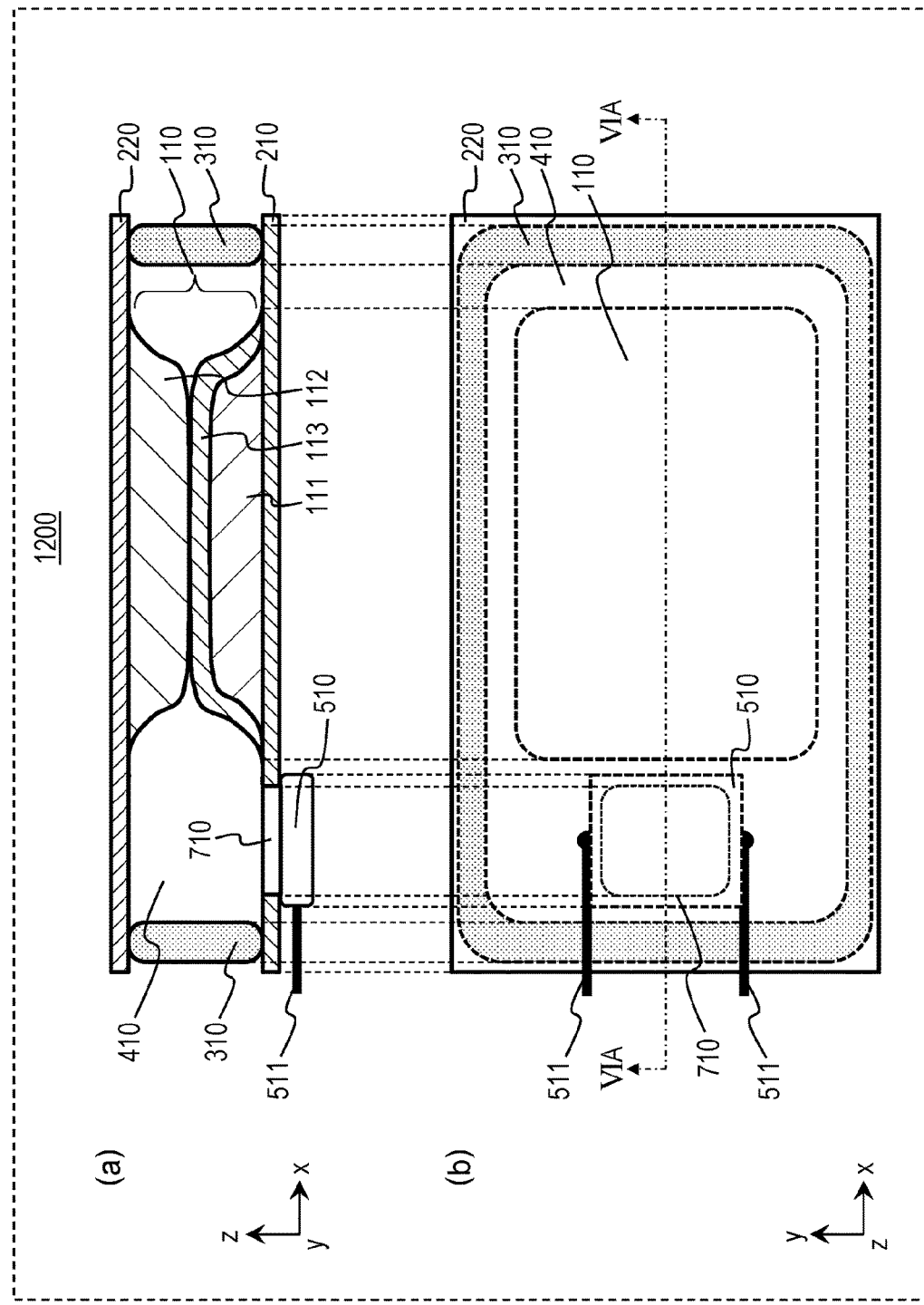
FIG. 6 is a schematic diagram illustrating the structure of a battery according to the first embodiment.

FIG. 6 is a schematic diagram illustrating a battery 1200 according to the first embodiment.

FIG. 6(a) is an x-z view illustrating the structure of the battery 1200 according to the first embodiment (sectional view taken along line VIA-VIA).

FIG. 6(b) is an x-y view (transparent top view) illustrating the structure of the battery 1200 according to the first embodiment.

In the battery 1200 according to the first embodiment, the first current collector 210 has a first communication hole 710.

One end of the first communication hole 710 is connected to a first void 410.

The first gas detection unit 510 covers the other end of the first communication hole 710.

According to the above-described structure, the first gas detection unit 510 can be disposed outside the first void 410 (for example, on a side of the first current collector 210 opposite to the side that is in contact with the first electrode layer 111). The gas in the first void 410 can be introduced into the first gas detection unit 510 disposed outside the first void 410 through the first communication hole 710. Even when the first gas detection unit 510 cannot be disposed inside the first void 410, the gas in the first void 410 can be detected by the first gas detection unit 510 disposed outside the first void 410.

In addition, according to the above-described structure, the process of arranging (enclosing) the first gas detection unit 510 in the first void 410 can be omitted. Also, a process of forming an additional structure, such as a first sensor chamber 810 described below, can be omitted. Therefore, the manufacturing process of the battery can be simplified.

In the battery 1200 according to the first embodiment, as illustrated in FIG. 6, the first communication hole 710 may be an opening smaller than the sensing region of the first gas detection unit 510.

Alternatively, the first communication hole 710 may instead be an opening larger than the sensing region of the first gas detection unit 510. In this case, the gap between the sensing region of the first gas detection unit 510 and the first communication hole 710 may be sealed with a sealing member or the like.

A member for reinforcing the connection between the first gas detection unit 510 and the first current collector 210 may be used when the first gas detection unit 510 covers one end of the first communication hole 710. In this case, the first gas detection unit 510 can be prevented from being separated (for example, peeled off) from the first current collector 210.

The member for reinforcing the connection between the first gas detection unit 510 and the first current collector 210 may be, for example, an adhesive. More specifically, the first gas detection unit 510 and the first current collector 210 may be bonded together by applying an adhesive to the contact portions of the first gas detection unit 510 and the first current collector 210.

Alternatively, the member for reinforcing the connection between the first gas detection unit 510 and the first current collector 210 may be, for example, a structure such as the first sensor chamber 810 described below.

Figure 7:
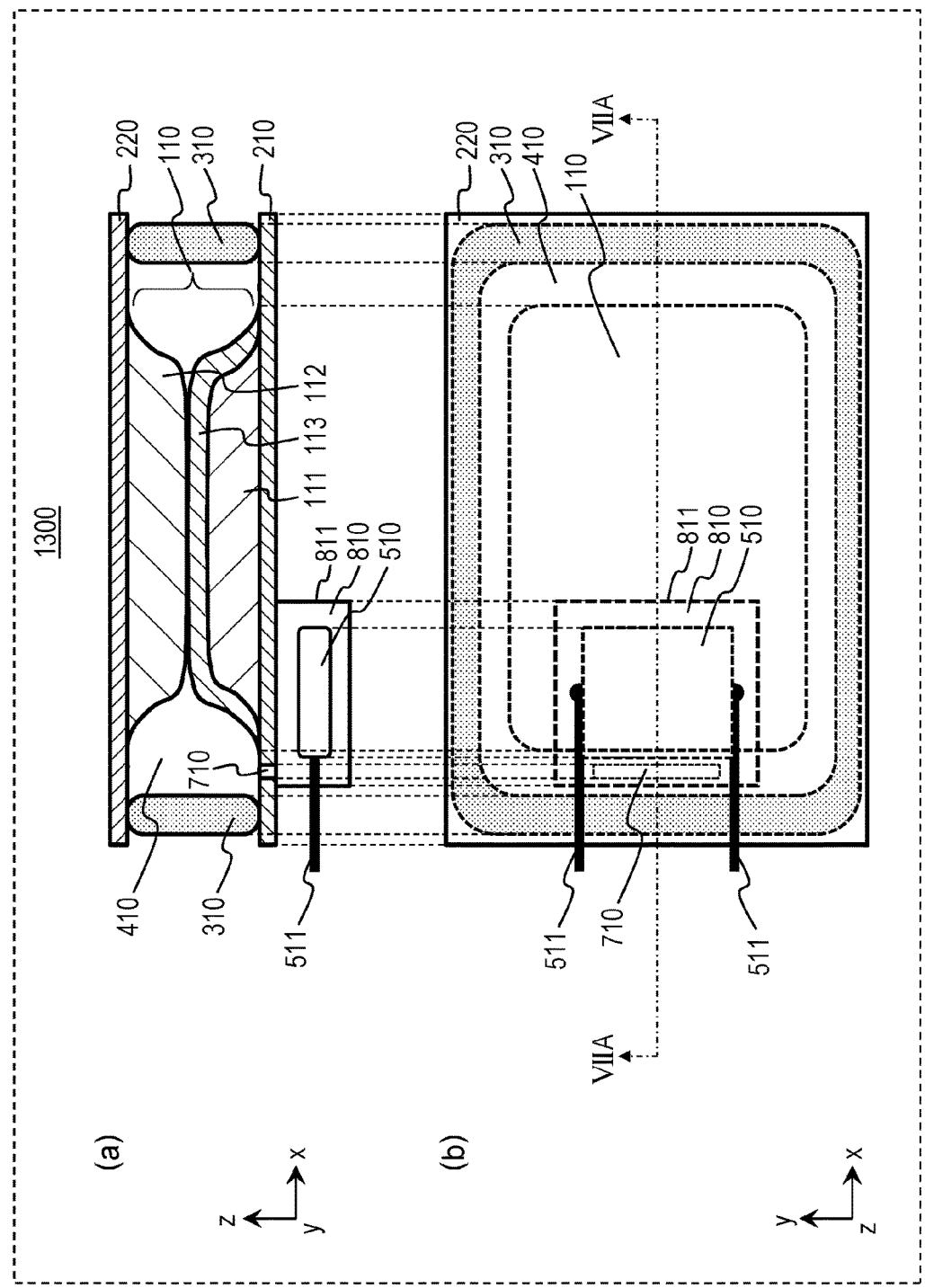
FIG. 7 is a schematic diagram illustrating the structure of a battery according to the first embodiment.

FIG. 7 is a schematic diagram illustrating a battery 1300 according to the first embodiment.

FIG. 7(a) is an x-z view illustrating the structure of the battery 1300 according to the first embodiment (sectional view taken along line VIIA-VIIA).

FIG. 7(b) is an x-y view (transparent top view) illustrating the structure of the battery 1300 according to the first embodiment.

The battery 1300 according to the first embodiment further includes a first sensor chamber 810.

The first gas detection unit 510 is disposed in the first sensor chamber 810.

The first current collector 210 has a first communication hole 710.

The first void 410 is connected to the first sensor chamber 810 through the first communication hole 710.

According to the above-described structure, the first gas detection unit 510 can be disposed outside the first void 410 (for example, on a side of the first current collector 210 opposite to the side that is in contact with the first electrode layer 111). The gas in the first void 410 can be introduced into the first gas detection unit 510 disposed outside the first void 410 through the first communication hole 710. Even when the first gas detection unit 510 cannot be disposed inside the first void 410, the gas in the first void 410 can be detected by the first gas detection unit 510 disposed outside the first void 410.

In addition, according to the above-described structure, the process of arranging (enclosing) the first gas detection unit 510 in the first void 410 can be omitted. Therefore, the manufacturing process of the battery can be simplified.

In the above-described structure, the size of the first communication hole 710 may be reduced within a range in which the gas can be introduced into the first sensor chamber 810. In other words, the size of the first communication hole 710 may be smaller than that in the case where the first gas detection unit 510 covers the first communication hole 710 (as in the above-described battery 1200). For example, the size of the first communication hole 710 may be smaller than the detection region of the first gas detection unit 510. Accordingly, in the first current collector 210, the area in which the first communication hole 710 is formed can be reduced. As a result, the size of the battery can be reduced.

As illustrated in FIG. 7, in the battery 1300 according to the first embodiment, the first sensor chamber 810 may be a space surrounded by a first sensor chamber wall 811.

The first sensor chamber wall 811 may be made of, for example, a commonly known material of an outer cover body of a battery.

In the battery 1300 according to the first embodiment, as illustrated in FIG. 7, the first sensor chamber 810 may be in contact with (and in parallel to) the first current collector 210. In this case, the principal surfaces of the first sensor chamber 810 may be smaller than the principal surfaces of the first current collector 210. Thus, the size of the space in which the gas is detected (that is, the first sensor chamber 810) can be reduced.

In the battery 1300 according to the first embodiment, as illustrated in FIG. 7, the size of the first sensor chamber 810 may be larger than the size of the sensing region of the first gas detection unit 510. More specifically, the sensing region of the first gas detection unit 510 may be surrounded by (for example, sealed by) the first sensor chamber wall 811. In this case, the first connection lines 511 connected to the first gas detection unit 510 may extend to the outside of the battery through the first sensor chamber wall 811.

In the case where the battery 1300 according to the first embodiment is accommodated in an outer cover body, the first sensor chamber 810 may be disposed inside the outer cover body. Alternatively, the first sensor chamber 810 may instead be disposed outside the outer cover body.

In the first embodiment, the first communication hole 710 may be a rectangular opening, as illustrated in FIGS. 6 and 7. Alternatively, the first communication hole 710 may be a circular opening. Alternatively, the first communication hole 710 may be a slit-shaped opening.

In the first embodiment, the first communication hole 710 may be formed as a single opening, as illustrated in FIGS. 6 and 7. Alternatively, the first communication hole 710 may be formed as a plurality of openings.

Second Embodiment

A second embodiment will now be described. Description of structures that are the same as those in the first embodiment will be omitted as appropriate.

Figure 8:
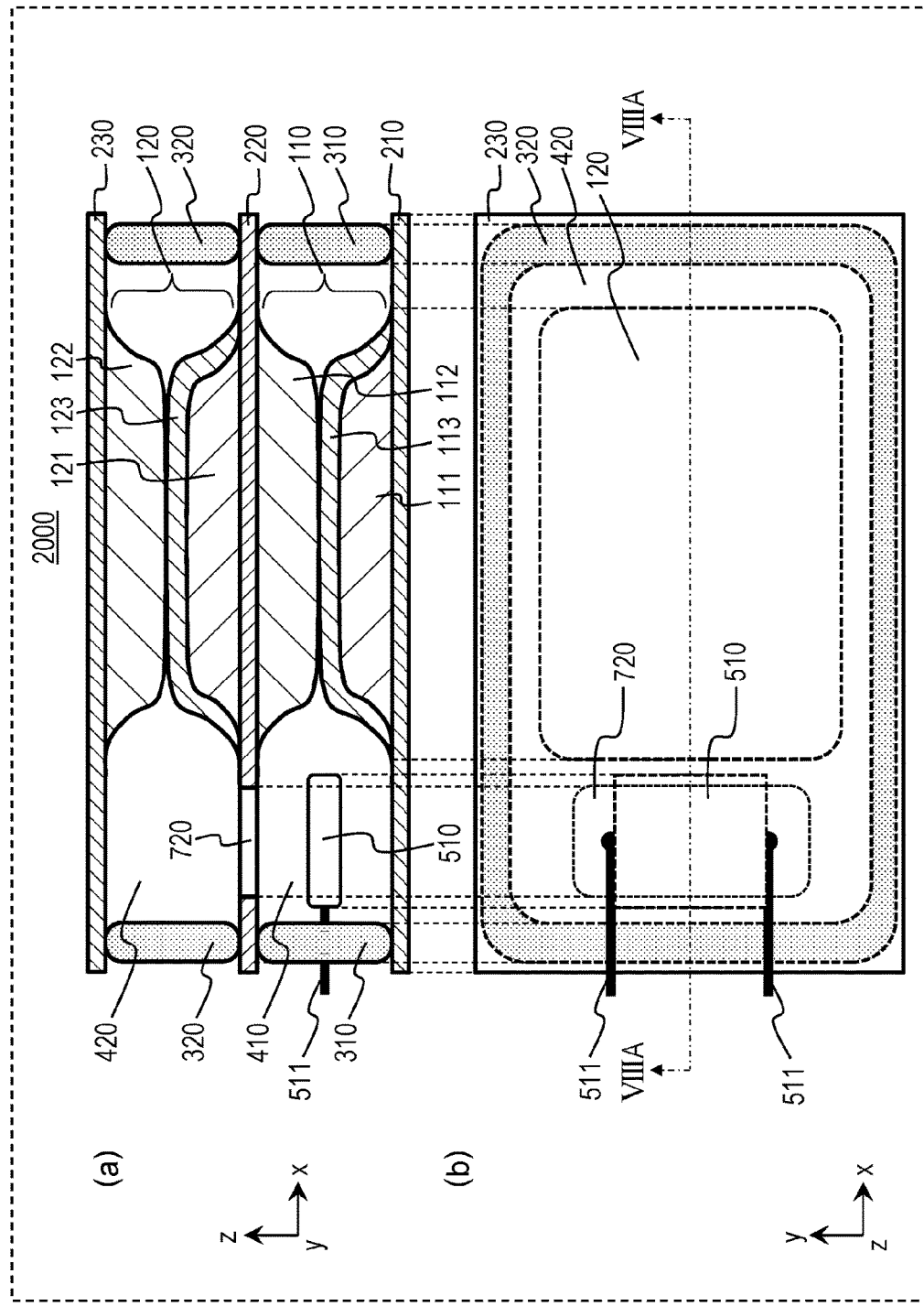
FIG. 8 is a schematic diagram illustrating the structure of a battery according to a second embodiment.

FIG. 8 is a schematic diagram illustrating a battery 2000 according to the second embodiment.

FIG. 8(a) is an x-z view illustrating the structure of the battery 2000 according to the second embodiment (sectional view taken along line VIIIA-VIIIA).

FIG. 8(b) is an x-y view (transparent top view) illustrating the structure of the battery 2000 according to the second embodiment.

The battery 2000 according to the second embodiment includes the following structure in addition to the structure of the battery according to the first embodiment.

More specifically, the battery 2000 according to the second embodiment additionally includes a second power generating element 120, a third current collector 230, a second sealing portion 320, and a second void 420.

The second power generating element 120 includes a second electrode layer 121 and a second counter electrode layer 122.

The second electrode layer 121 is in contact with the second current collector 220.

The third current collector 230 is in contact with the second counter electrode layer 122.

The second sealing portion 320 seals the gap between the second current collector 220 and the third current collector 230.

The second void 420 is disposed between the second sealing portion 320 and the second power generating element 120.

The second current collector 220 has a second communication hole 720.

The second communication hole 720 connects the first void 410 to the second void 420.

According to the above-described structure, gas generated by the second power generating element 120 can be introduced into the first void 410 through the second void 420 and the second communication hole 720. Accordingly, the gas generated by the second power generating element 120 can be detected by the first gas detection unit 510 in the first void 410. Therefore, it is not necessary to use a gas detection sensor for detecting the gas generated by the second power generating element 120 in addition to the first gas detection unit 510. Thus, the number of gas detection sensors can be reduced. Since the number of gas detection sensors can be reduced, the process of arranging (enclosing) multiple gas detection sensors in the battery can be omitted. Accordingly, the manufacturing process of the battery can be simplified. As a result, the gas detection structure can be more easily installed in the battery at a lower cost. In addition, a reduction in reliability, which occurs when multiple gas detection sensors are sealed, can be prevented. Also, it is not necessary to arrange connection lines for the multiple gas detection sensors or process detection signals from the gas detection sensors. This prevents the battery structure from becoming complex. Thus, the structure and manufacturing process of the battery can be simplified.

According to the above-described structure, gas can be detected at high detection sensitivity. More specifically, the second sealing portion 320 limits the space accommodating the second power generating element 120, which may generate gas, to the second void 420, which is a small space. Thus, the second void 420 and the first void 410, which are small spaces, serve as a detection space in which the gas is detected. Accordingly, unlike the case in which the detection space is a larger space in the battery (for example, the space inside an outer cover body), the gas generated by the first power generating element 110 and the gas generated by the second power generating element 120 can be prevented from being dissipated and diluted in the larger space. The gas generated by the first power generating element 110 and the gas generated by the second power generating element 120 remain in a smaller space, that is, in the first void 410 and the second void 420. Therefore, the first gas detection unit 510 can detect "the gas in the first void 410" (gas generated in the first void 410 and gas generated in the second void 420 and entered the first void 410) at an early stage while the concentration of the gas is high. As a result, the gas detection sensitivity can be increased.

In addition, according to the above-described structure, the safety of the battery can be increased. More specifically, the regions around the first power generating element 110 and the second power generating element 120, which may generate gas, are surrounded (for example, sealed) by the first sealing portion 310 and the second sealing portion 320, respectively. When, for example, the battery further includes an outer cover body, the outer cover body, the first sealing portion 310, and the second sealing portion 320 form a multilayer safety structure. Accordingly, the gas generated by the first power generating element 110 and the gas generated by the second power generating element 120 are prevented from being immediately dissipated in the space inside the battery (for example, the space inside the outer cover body) or to the outside of the battery. Therefore, even if the sealed outer cover body is fractured or corroded when the gas is detected, the risk of leakage of harmful gas (for example, hydrogen sulfide gas) to the outside of the battery can be considerably reduced. Thus, the safety of the battery can be increased.

The second electrode layer 121 contains a second electrode material.

The second counter electrode layer 122 serves as a counter electrode for the second electrode layer 121. The second counter electrode layer 122 contains a second counter electrode material.

In the second power generating element 120, one of the second electrode layer 121 and the second counter electrode layer 122 is a positive electrode layer, and the other is a negative electrode layer.

When, for example, the first electrode layer 111 is a positive electrode layer, the second electrode layer 121 is a positive electrode layer. In this case, the second electrode material is a positive electrode material. The second counter electrode layer 122 is a negative electrode layer. The second counter electrode material is a negative electrode material. The third current collector 230 is a negative electrode current collector.

When, for example, the first electrode layer 111 is a negative electrode layer, the second electrode layer 121 is a negative electrode layer. In this case, the second electrode material is a negative electrode material. The second counter electrode layer 122 is a positive electrode layer. The second counter electrode material is a positive electrode material. The third current collector 230 is a positive electrode current collector.

In the battery 2000 according to the second embodiment, as illustrated in FIG. 8, the second power generating element 120 may include a second solid electrolyte layer 123.

The second solid electrolyte layer 123 is disposed between the second electrode layer 121 and the second counter electrode layer 122.

At least one of the second electrode layer 121, the second counter electrode layer 122, and the second solid electrolyte layer 123 may contain a second sulfur-based material (for example, the above-described sulfide solid electrolyte).

The gas may contain hydrogen sulfide gas generated due to the second sulfur-based material.

In the second embodiment, the material, shape, size, etc., of the second power generating element 120 may be the same as those of the first power generating element 110. Alternatively, one or more of the material, shape, size, etc., of the second power generating element 120 may differ from those of the first power generating element 110.

In the second embodiment, the second current collector 220 is a bipolar current collector having a positive electrode layer and a negative electrode layer on the front and back surfaces thereof.

Examples of the material of the second sealing portion 320 are the same as the above-described examples of the material of the first sealing portion 310.

As illustrated in FIG. 8, the second sealing portion 320 may seal the periphery (for example, four sides) of the second power generating element 120.

The second void 420 is at least a void (space) disposed between the second sealing portion 320 and the second power generating element 120.

More specifically, similar to the above-described first void 410, the expression "the second void 420 is disposed between the second sealing portion 320 and the second power generating element 120" includes the case in which "the second void 420 is disposed between (surrounded by) the second sealing portion 320, the second power generating element 120, and other components.

As illustrated in FIG. 8, the second void 420 may be formed at the periphery (for example, four sides) of the second power generating element 120.

Figure 9:
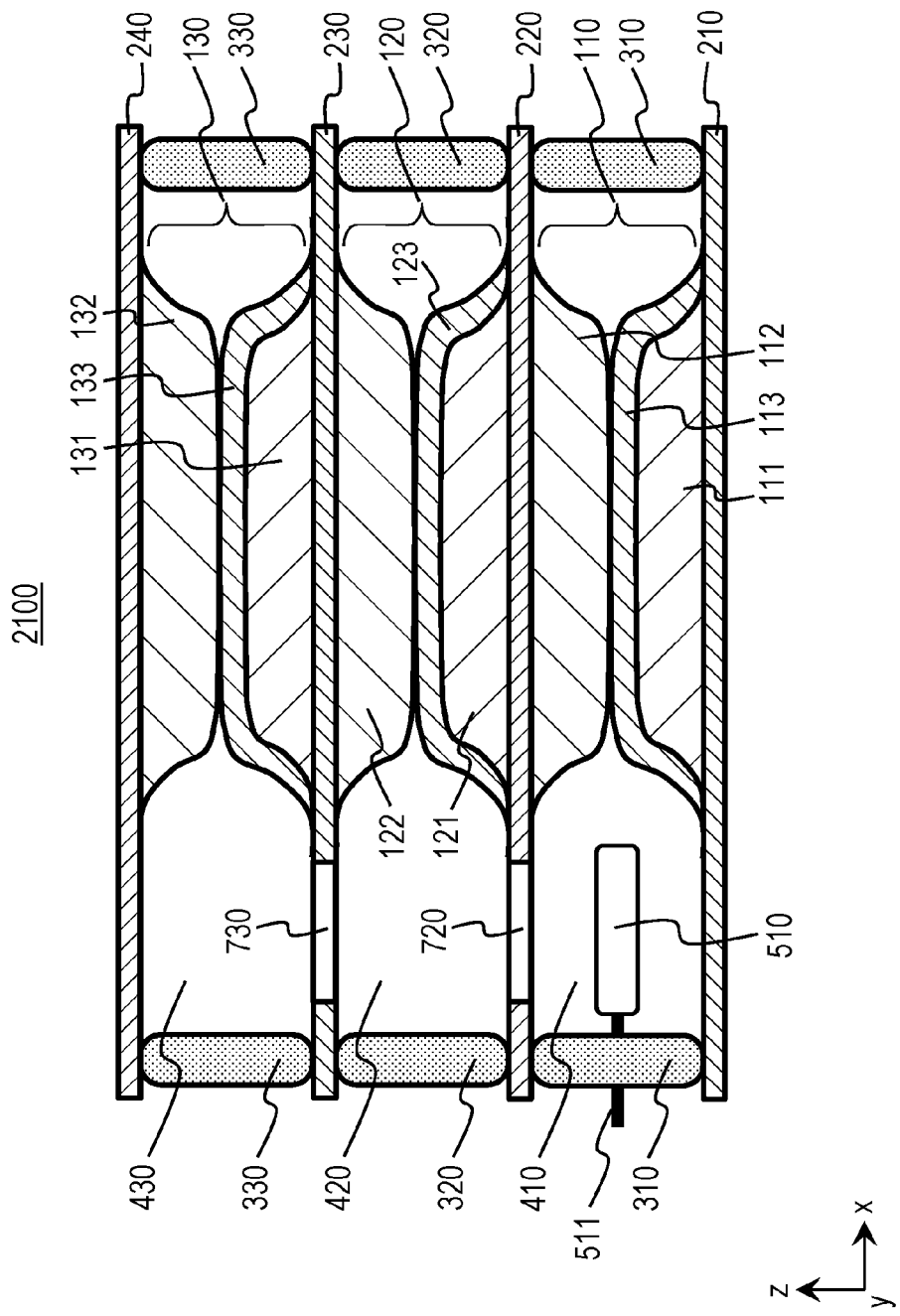
FIG. 9 is a schematic sectional view illustrating the structure of a battery according to the second embodiment.

FIG. 9 is a schematic sectional view illustrating the structure of a battery 2100 according to the second embodiment.

The battery 2100 according to the second embodiment includes the following structure in addition to the structure of the battery 2000.

More specifically, the battery 2100 according to the second embodiment additionally includes a third power generating element 130, a fourth current collector 240, a third sealing portion 330, and a third void 430.

The third power generating element 130 includes a third electrode layer 131 and a third counter electrode layer 132.

The third electrode layer 131 is in contact with the third current collector 230.

The fourth current collector 240 is in contact with the third counter electrode layer 132.

The third sealing portion 330 seals the gap between the third current collector 230 and the fourth current collector 240.

The third void 430 is disposed between the third sealing portion 330 and the third power generating element 130.

The third current collector 230 has a third communication hole 730.

The third communication hole 730 connects the second void 420 to the third void 430.

According to the above-described structure, gas generated by the third power generating element 130 can be introduced into the first void 410 through the third void 430, the third communication hole 730, the second void 420, and the second communication hole 720. Accordingly, the gas generated by the third power generating element 130 can be detected by the first gas detection unit 510 in the first void 410. Therefore, it is not necessary to use a gas detection sensor for detecting the gas generated by the third power generating element 130 in addition to the first gas detection unit 510. Thus, the number of gas detection sensors can be reduced. Since the number of gas detection sensors can be reduced, the process of arranging (enclosing) multiple gas detection sensors in the battery can be omitted. Accordingly, the manufacturing process of the battery can be simplified. As a result, the gas detection structure can be more easily installed in the battery at a lower cost. In addition, a reduction in reliability, which occurs when multiple gas detection sensors are sealed, can be prevented. Also, it is not necessary to arrange connection lines for the multiple gas detection sensors or process detection signals from the gas detection sensors. This prevents the battery structure from becoming complex. Thus, the structure and manufacturing process of the battery can be simplified.

According to the above-described structure, gas can be detected at high detection sensitivity. More specifically, the third sealing portion 330 limits the space accommodating the third power generating element 130, which may generate gas, to the third void 430, which is a small space. Thus, the third void 430, the second void 420, and the first void 410, which are small spaces, serve as a detection space in which the gas is detected. Accordingly, unlike the case in which the detection space is a larger space in the battery (for example, the space inside an outer cover body), the gas generated by the first power generating element 110, the gas generated by the second power generating element 120, and the gas generated by the third power generating element 130 can be prevented from being dissipated and diluted in the larger space. The gas generated by the first power generating element 110, the gas generated by the second power generating element 120, and the gas generated by the third power generating element 130 remain in the small spaces, that is, in the first void 410, the second void 420, and the third void 430. Therefore, the first gas detection unit 510 can detect "the gas in the first void 410" (gas generated in the first void 410, gas generated in the second void 420 and entered the first void 410, and gas generated in the third void 430 and entered the first void 410) at an early stage while the concentration of the gas is high. As a result, the gas detection sensitivity can be increased.

In addition, according to the above-described structure, the safety of the battery can be increased. More specifically, the regions around the first power generating element 110, the second power generating element 120, and the third power generating element 130, which may generate gas, are surrounded (for example, sealed) by the first sealing portion 310, the second sealing portion 320, and the third sealing portion 330, respectively. When, for example, the battery further includes an outer cover body, the outer cover body, the first sealing portion 310, the second sealing portion 320, and the third sealing portion 330 form a multilayer safety structure. Accordingly, the gas generated by the first power generating element 110, the gas generated by the second power generating element 120, and the gas generated by the third power generating element 130 are prevented from being immediately dissipated in the space inside the battery (for example, the space inside the outer cover body) or to the outside of the battery. Therefore, even if the sealed outer cover body is fractured or corroded when the gas is detected, the risk of leakage of harmful gas (for example, hydrogen sulfide gas) to the outside of the battery can be considerably reduced. Thus, the safety of the battery can be increased.

The third electrode layer 131 contains a third electrode material.

The third counter electrode layer 132 serves as a counter electrode for the third electrode layer 131. The third counter electrode layer 132 contains a third counter electrode material.

In the third power generating element 130, one of the third electrode layer 131 and the third counter electrode layer 132 is a positive electrode layer, and the other is a negative electrode layer.

When, for example, the first electrode layer 111 is a positive electrode layer, the second electrode layer 121 and the third electrode layer 131 are positive electrode layers. In this case, the third electrode material is a positive electrode material. The third counter electrode layer 132 is a negative electrode layer. The third counter electrode material is a negative electrode material. The fourth current collector 240 is a negative electrode current collector.

When, for example, the first electrode layer 111 is a negative electrode layer, the second electrode layer 121 and the third electrode layer 131 are negative electrode layers. In this case, the third electrode material is a negative electrode material. The third counter electrode layer 132 is a positive electrode layer. The third counter electrode material is a positive electrode material. The fourth current collector 240 is a positive electrode current collector.

In the battery 2100 according to the second embodiment, as illustrated in FIG. 9, the third power generating element 130 may include a third solid electrolyte layer 133.

The third solid electrolyte layer 133 is disposed between the third electrode layer 131 and the third counter electrode layer 132.

At least one of the third electrode layer 131, the third counter electrode layer 132, and the third solid electrolyte layer 133 may contain a third sulfur-based material (for example, the above-described sulfide solid electrolyte).

The gas may contain hydrogen sulfide gas generated due to the third sulfur-based material.

In the second embodiment, the material, shape, size, etc., of the third power generating element 130 may be the same as those of the first power generating element 110 or the second power generating element 120. Alternatively, one or more of the material, shape, size, etc., of the third power generating element 130 may differ from those of the first power generating element 110 or the second power generating element 120.

In the second embodiment, the third current collector 230 is a bipolar current collector having a positive electrode layer and a negative electrode layer on the front and back surfaces thereof.

Examples of the material of the third sealing portion 330 are the same as the above-described examples of the material of the first sealing portion 310.

The third sealing portion 330 may seal the periphery (for example, four sides) of the third power generating element 130.

The third void 430 is at least a void (space) disposed between the third sealing portion 330 and the third power generating element 130.

More specifically, similar to the above-described first void 410, the expression "the third void 430 is disposed between the third sealing portion 330 and the third power generating element 130" includes the case in which "the third void 430 is disposed between (surrounded by) the third sealing portion 330, the third power generating element 130, and other components.

The third void 430 may be formed at the periphery (for example, four sides) of the third power generating element 130.

Figure 10:
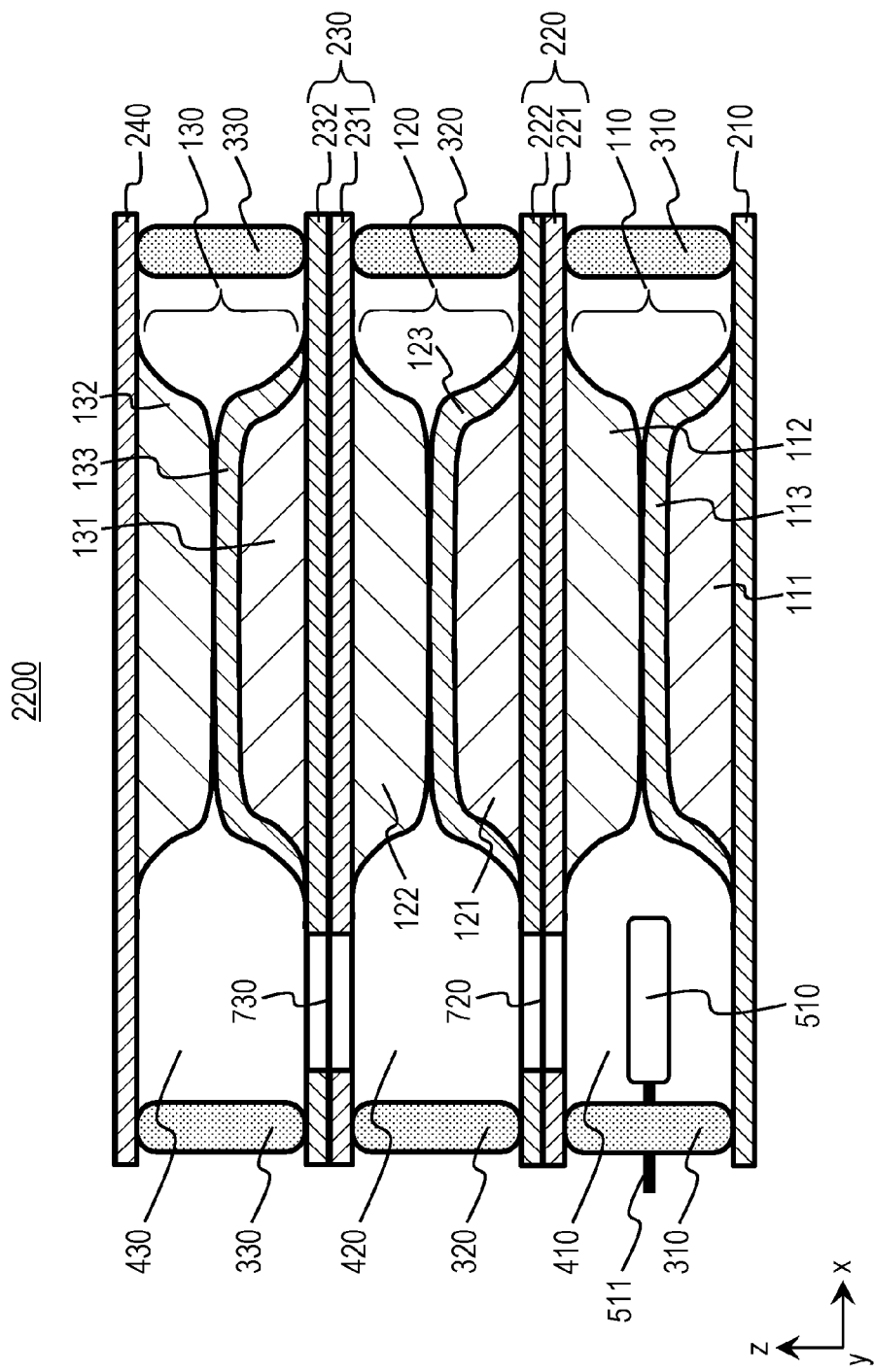
FIG. 10 is a schematic sectional view illustrating the structure of a battery according to the second embodiment.

FIG. 10 is a schematic sectional view illustrating the structure of a battery 2200 according to the second embodiment.

In the second embodiment, as illustrated in FIG. 10, the second current collector 220 may include current collectors 221 and 222.

One of the current collectors 221 and 222 is a positive electrode current collector, and the other is a negative electrode current collector.

When, for example, the first counter electrode layer 112 is a positive electrode layer, the current collector 221 is a positive electrode current collector. In this case, the current collector 222 is a negative electrode current collector.

When the first counter electrode layer 112 is a negative electrode layer, the current collector 221 is a negative electrode current collector. In this case, the current collector 222 is a positive electrode current collector.

An adhesive may be applied between the current collectors 221 and 222 over portions thereof or over the entire areas thereof. Thus, the second current collector 220 may be formed by joining the current collectors 221 and 222 together.

As illustrated in FIG. 10, the current collectors 221 and 222 each have an opening. The second communication hole 720 may be formed by aligning these openings.

In the second embodiment, as illustrated in FIG. 10, the third current collector 230 may include current collectors 231 and 232.

One of the current collectors 231 and 232 is a positive electrode current collector, and the other is a negative electrode current collector.

When, for example, the second counter electrode layer 122 is a positive electrode layer, the current collector 231 is a positive electrode current collector. In this case, the current collector 232 is a negative electrode current collector.

When the second counter electrode layer 122 is a negative electrode layer, the current collector 231 is a negative electrode current collector. In this case, the current collector 232 is a positive electrode current collector.

An adhesive may be applied between the current collectors 231 and 232 over portions thereof or the entire areas thereof. Thus, the third current collector 230 may be formed by joining the current collectors 231 and 232.

As illustrated in FIG. 10, the current collectors 231 and 232 each have an opening. The third communication hole 730 may be formed by aligning these openings.

Figure 11:
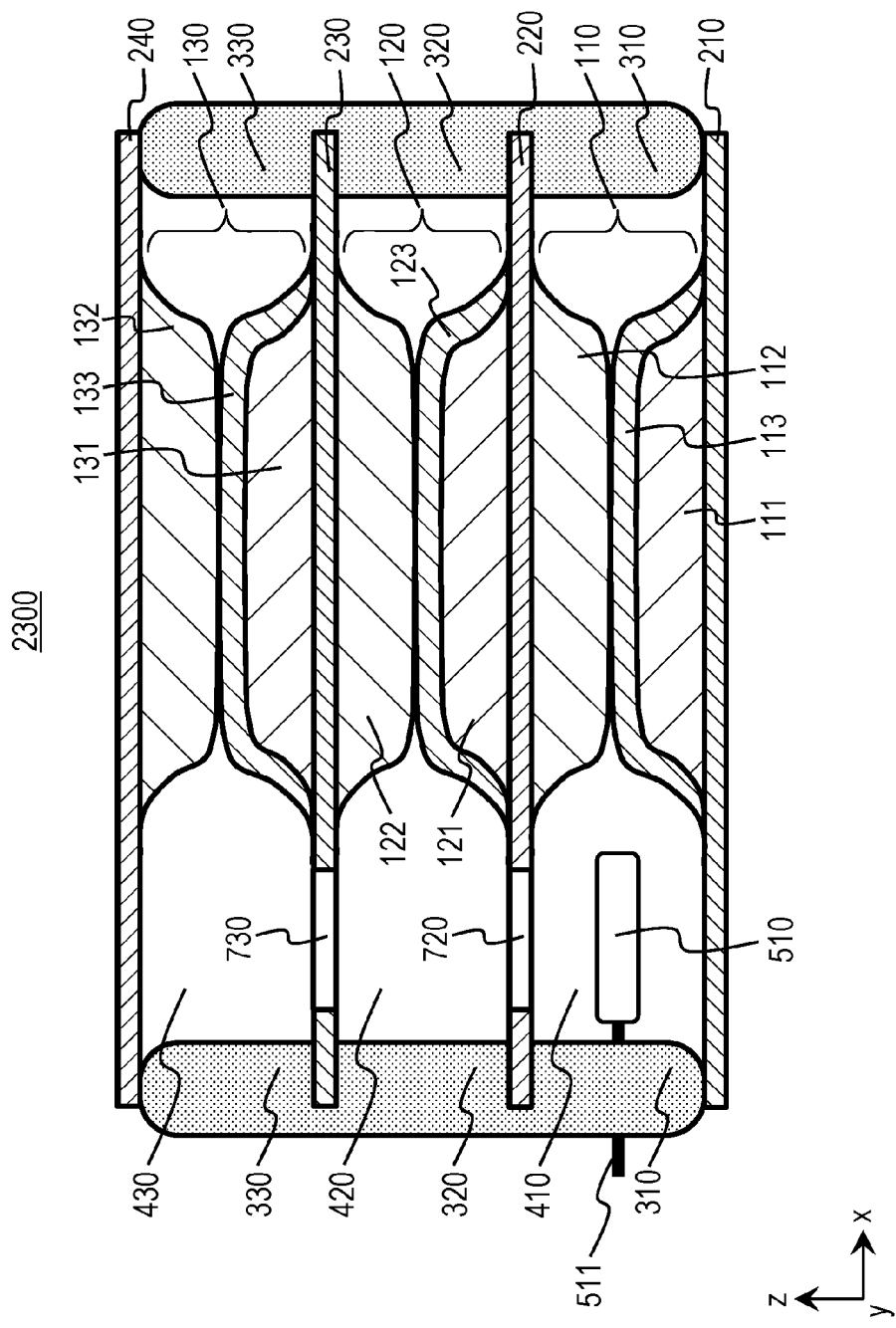
FIG. 11 is a schematic sectional view illustrating the structure of a battery according to the second embodiment.

FIG. 11 is a schematic sectional view illustrating the structure of a battery 2300 according to the second embodiment.

In the second embodiment, as illustrated in FIG. 11, the first sealing portion 310, the second sealing portion 320, and the third sealing portion 330 may be formed as a sealing portion having an integral structure. For example, the first sealing portion 310, the second sealing portion 320, and the third sealing portion 330 may be formed together as a single sealing portion. In this case, the sealing process is easier than in the case where the first sealing portion 310, the second sealing portion 320, and the third sealing portion 330 are formed individually.

Figure 12:
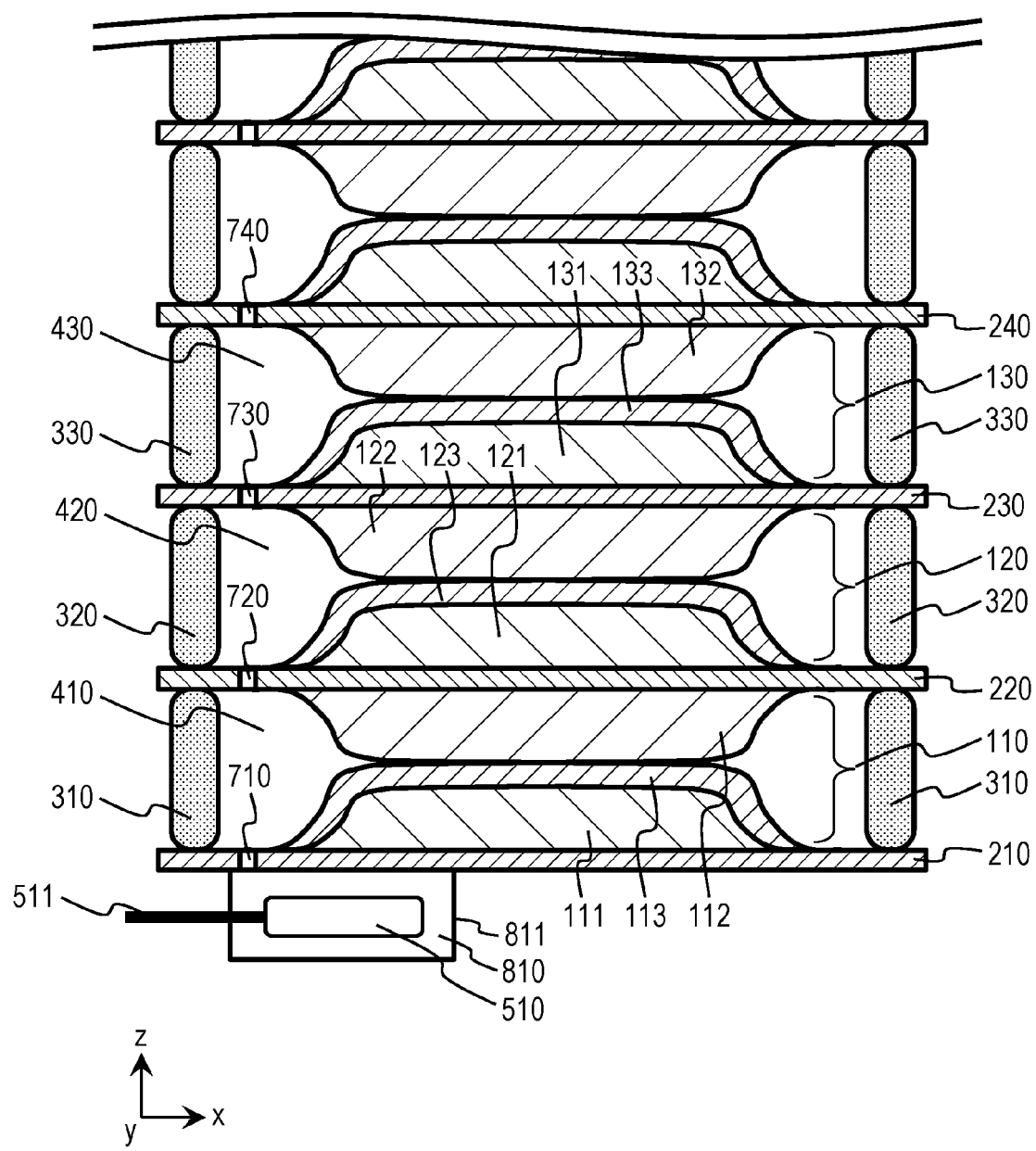
FIG. 12 is a schematic sectional view illustrating the structure of a battery according to the second embodiment.

FIG. 12 is a schematic sectional view illustrating the structure of a battery 2400 according to the second embodiment.

In the second embodiment, as illustrated in FIG. 12, the battery may be formed by stacking four or more power generating elements.

In the battery 2400 illustrated in FIG. 12, the fourth and following power generating elements are stacked on the fourth current collector 240. Each of the fourth and following power generating elements is sealed by a sealing portion at the periphery thereof. Accordingly, fourth and following voids are formed between the fourth and following power generating elements and the corresponding sealing portions.

In the battery 2400 illustrated in FIG. 12, the fourth current collector 240 has a fourth communication hole 740. In addition, each of the current collectors disposed above the fourth current collector 240 also has a communication hole. Thus, the third void 430 is connected to the fourth and following voids.

As described above, the battery according to the second embodiment may be a bipolar battery in which a plurality of power generating elements (electric cells) are connected in series.

The bipolar battery (bipolar all-solid battery) may be formed by stacking bipolar current collectors, each having a positive electrode layer and a negative electrode layer on the front and back surfaces thereof, with solid electrolyte layers interposed therebetween. The power generating elements may be compressed in this state. Thus, the power generating elements can be more reliably arranged and connected in series.

A high voltage, for example, can be obtained by using the bipolar battery in which a plurality of power generating elements (electric cells) are connected in series.

The number of power generating elements stacked in the battery according to the second embodiment may be, for example, 2 to 200. The output of the battery may be adjusted in accordance with the usage (electronic device, electrical appliance, electric vehicle, stationary battery, etc.) by adjusting the number of power generating elements that are stacked.

In the second embodiment, the second communication hole 720, the third communication hole 730, and the fourth communication hole 740 may be rectangular openings. Alternatively, the second communication hole 720, the third communication hole 730, and the fourth communication hole 740 may be circular openings. Alternatively, the second communication hole 720, the third communication hole 730, and the fourth communication hole 740 may be slit-shaped openings.

In the second embodiment, each of the second communication hole 720, the third communication hole 730, and the fourth communication hole 740 may be formed as a single opening. Alternatively, each of the second communication hole 720, the third communication hole 730, and the fourth communication hole 740 may be formed as a plurality of openings.

In the second embodiment, the first communication hole 710, the second communication hole 720, the third communication hole 730, and the fourth communication hole 740 may have either the same shape and size, or different shapes and sizes.

The communication holes in the current collectors may have a size (opening area) of 100 $\mu m^2$ to 1 $cm^2$.

Alternatively, the communication holes in the current collectors may have a size (opening area) of 0.01 $mm^2$ to 25 $mm^2$. In this case, an increase in processing cost, a degradation of current collecting property, a reduction in durability, etc., can be prevented.

In the second embodiment, the arrangement and structure of the first gas detection unit 510 may be the same as those in the first embodiment illustrated in FIGS. 1 to 7.

In the second embodiment, the gas detection space is increased since the voids are connected to each other. However, the increase in the gas detection space is sufficiently small in practical all-solid batteries. Therefore, the detection sensitivity of the first gas detection unit 510 is not significantly reduced.

In the second embodiment, the first gas detection unit 510 may be disposed at the bottom of the battery. In this case, the gas generated in each void is introduced into the first gas detection unit 510, which is disposed at the bottom of the battery, through the communication holes formed in the current collectors.

According to the above-described structure, even when a lower section of the battery is filled with gas (for example, hydrogen sulfide gas that is heavier than atmospheric air) that is generated when external gas (for example, atmospheric air) enters the battery, the gas that fills the lower section of the battery can be detected by the first gas detection unit 510 disposed at the bottom of the battery. Therefore, the first gas detection unit 510 can detect "the gas in each void" at an early stage while the concentration of the gas is high. As a result, the gas detection sensitivity can be increased.

Third Embodiment

A third embodiment will now be described. Description of structures that are the same as those in the first or second embodiment will be omitted as appropriate.

Figure 13:
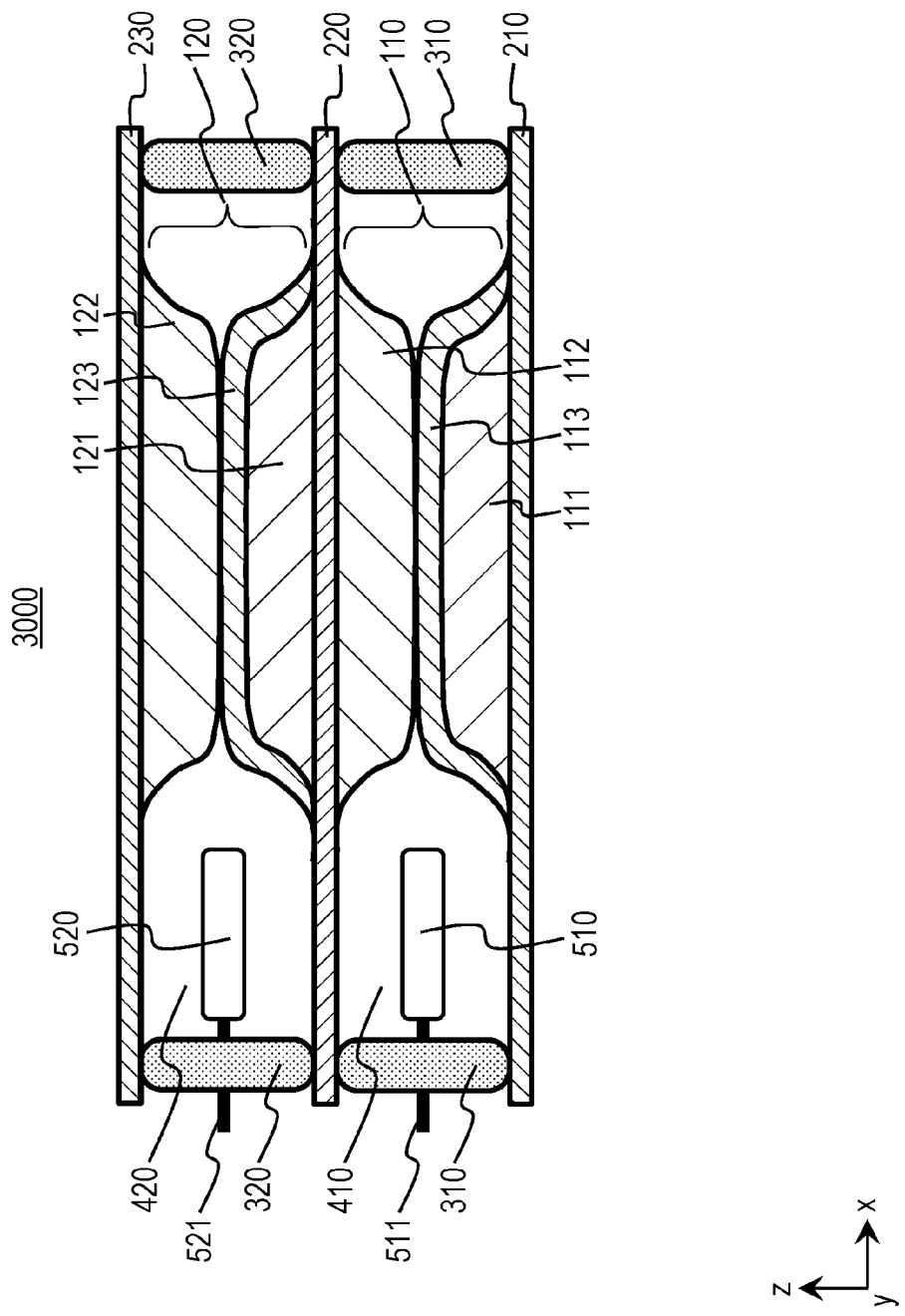
FIG. 13 is a schematic sectional view illustrating the structure of a battery according to a third embodiment.

FIG. 13 is a schematic sectional view illustrating the structure of a battery 3000 according to the third embodiment.

The battery 3000 according to the third embodiment includes the following structure in addition to the structure of the battery according to the first embodiment.

More specifically, the battery 3000 according to the third embodiment additionally includes a second power generating element 120, a third current collector 230, a second sealing portion 320, a second void 420, and a second gas detection unit 520.

The second power generating element 120 includes a second electrode layer 121 and a second counter electrode layer 122.

The second electrode layer 121 is in contact with the second current collector 220.

The third current collector 230 is in contact with the second counter electrode layer 122.

The second sealing portion 320 seals the gap between the second current collector 220 and the third current collector 230.

The second void 420 is disposed between the second sealing portion 320 and the second power generating element 120.

The second gas detection unit 520 detects "gas in the second void 420."

According to the above-described structure, the gas generated in the first void 410 and the gas generated in the second void 420 can be accurately detected by the first gas detection unit 510 and the second gas detection unit 520, respectively.

According to the above-described structure, gas (for example, hydrogen sulfide gas) can be detected at high detection sensitivity. More specifically, the second sealing portion 320 limits the space accommodating the second power generating element 120, which may generate gas, to the second void 420, which is a small space. Thus, the second void 420, which is a small space, serves as a detection space in which the gas is detected. Accordingly, unlike the case in which the detection space is a larger space in the battery (for example, the space inside an outer cover body), the gas generated by the second power generating element 120 can be prevented from being dissipated and diluted in the larger space. The gas generated by the second power generating element 120 remains in a smaller space, that is, in the second void 420. Therefore, the second gas detection unit 520 can detect "the gas in the second void 420" at an early stage while the concentration of the gas is high. As a result, the gas detection sensitivity can be increased.

In addition, according to the above-described structure, the safety of the battery can be increased. More specifically, the regions around the first power generating element 110 and the second power generating element 120, which may generate gas, are surrounded (for example, sealed) by the first sealing portion 310 and the second sealing portion 320, respectively. When, for example, the battery further includes an outer cover body, the outer cover body, the first sealing portion 310, and the second sealing portion 320 form a multilayer safety structure. Accordingly, the gas generated by the first power generating element 110 and the gas generated by the second power generating element 120 are prevented from being immediately dissipated in the space inside the battery (for example, the space inside the outer cover body) or to the outside of the battery. Therefore, even if the sealed outer cover body is fractured or corroded when the gas is detected, the risk of leakage of harmful gas (for example, hydrogen sulfide gas) to the outside of the battery can be considerably reduced. Thus, the safety of the battery can be increased.

The structure, shape, and material of the above-described first gas detection unit 510 may be used as those of the second gas detection unit 520.

The structure, shape, and material of the second gas detection unit 520 may be the same as or different from those of the first gas detection unit 510.

In the battery 3000 according to the third embodiment, as illustrated in FIG. 13, the second gas detection unit 520 may be disposed in the second void 420.

According to the above-described structure, the gas detection sensitivity can be increased. More specifically, the gas generated by the second power generating element 120 and remaining in the second void 420 can be detected in the second void 420. Therefore, the second gas detection unit 520 can detect the gas in the second void 420 at an early stage while the concentration of the gas is high.

Referring to FIG. 13, the battery 3000 according to the third embodiment may further include two second connection lines 521.

The second gas detection unit 520 may have a sensing region (for example, a portion formed of a resistance variable material) that is connected to one end of each of the two second connection lines 521.

In the battery 3000 according to the third embodiment, the other end of each of the two second connection lines 521 extends to, for example, the outside of the battery 3000 through the second sealing portion 320.

The two second connection lines 521 that extend to the outside of the battery 3000 may be connected to a detection device for detecting gas. The detection device may or may not be the same device as the detection device to which the first connection lines 511 are connected (in other words, to which the first gas detection unit 510 is connected).

Figure 14:
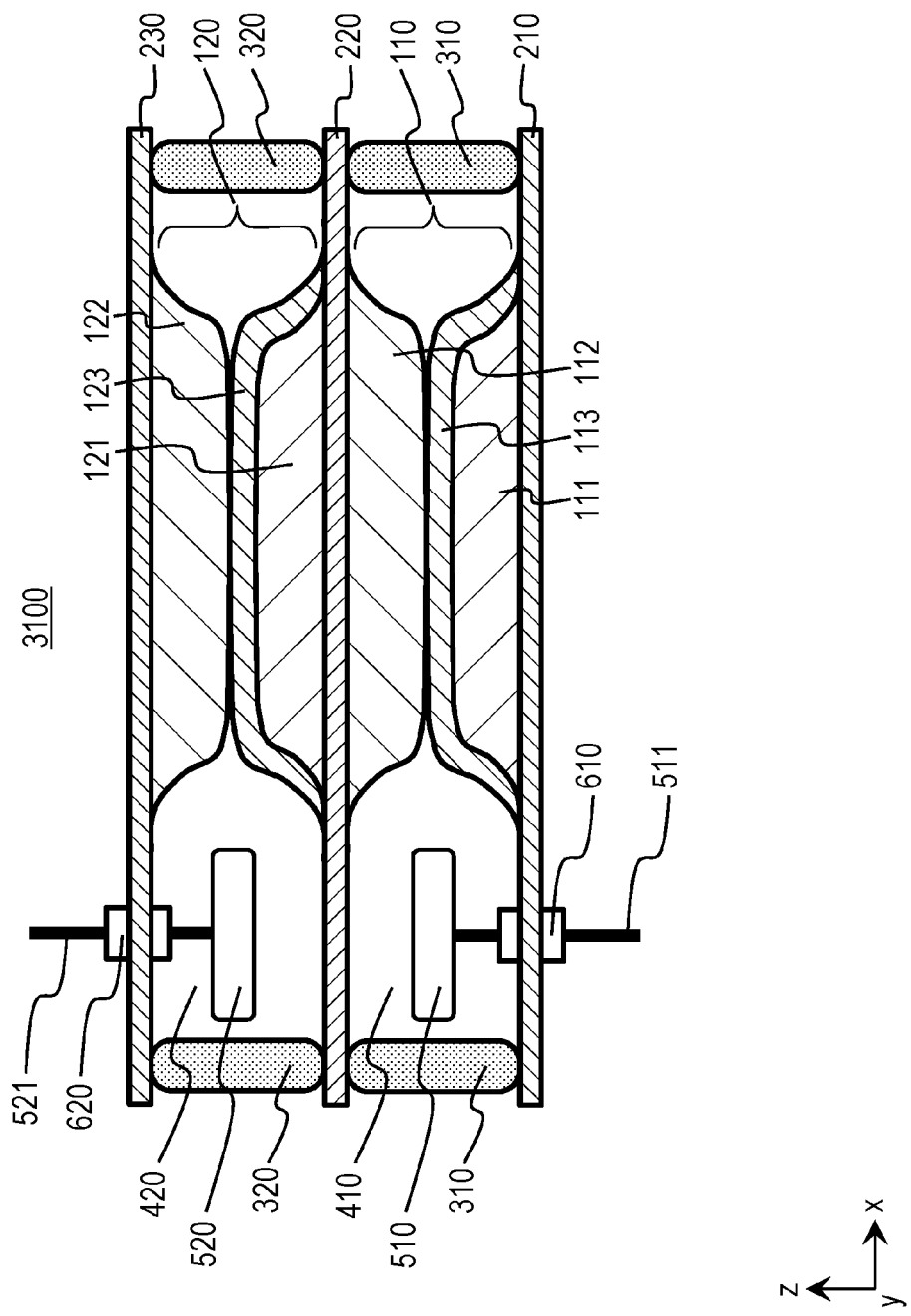
FIG. 14 is a schematic sectional view illustrating the structure of a battery according to the third embodiment.

FIG. 14 is a schematic sectional view illustrating the structure of a battery 3100 according to the third embodiment.

In the battery 3100 according to the third embodiment, the third current collector 230 includes second passage portions 620.

The second gas detection unit 520 includes the second connection lines 521.

The second connection lines 521 extend to the outside through the second passage portions 620.

According to the above-described structure, the structure for enabling the second connection lines 521 of the second gas detection unit 520 to extend to the outside can be more easily formed than in the case where the second connection lines 521 extend to the outside through the second sealing portion 320 (as in the above-described battery 3000).

Each second passage portion 620 may include, for example, an opening formed in the third current collector 230 and a sealing portion that seals the gap between the opening and the corresponding second connection line 521. The material of the sealing portion may be the same as the material of the above-described first sealing portion 310.

Figure 15:
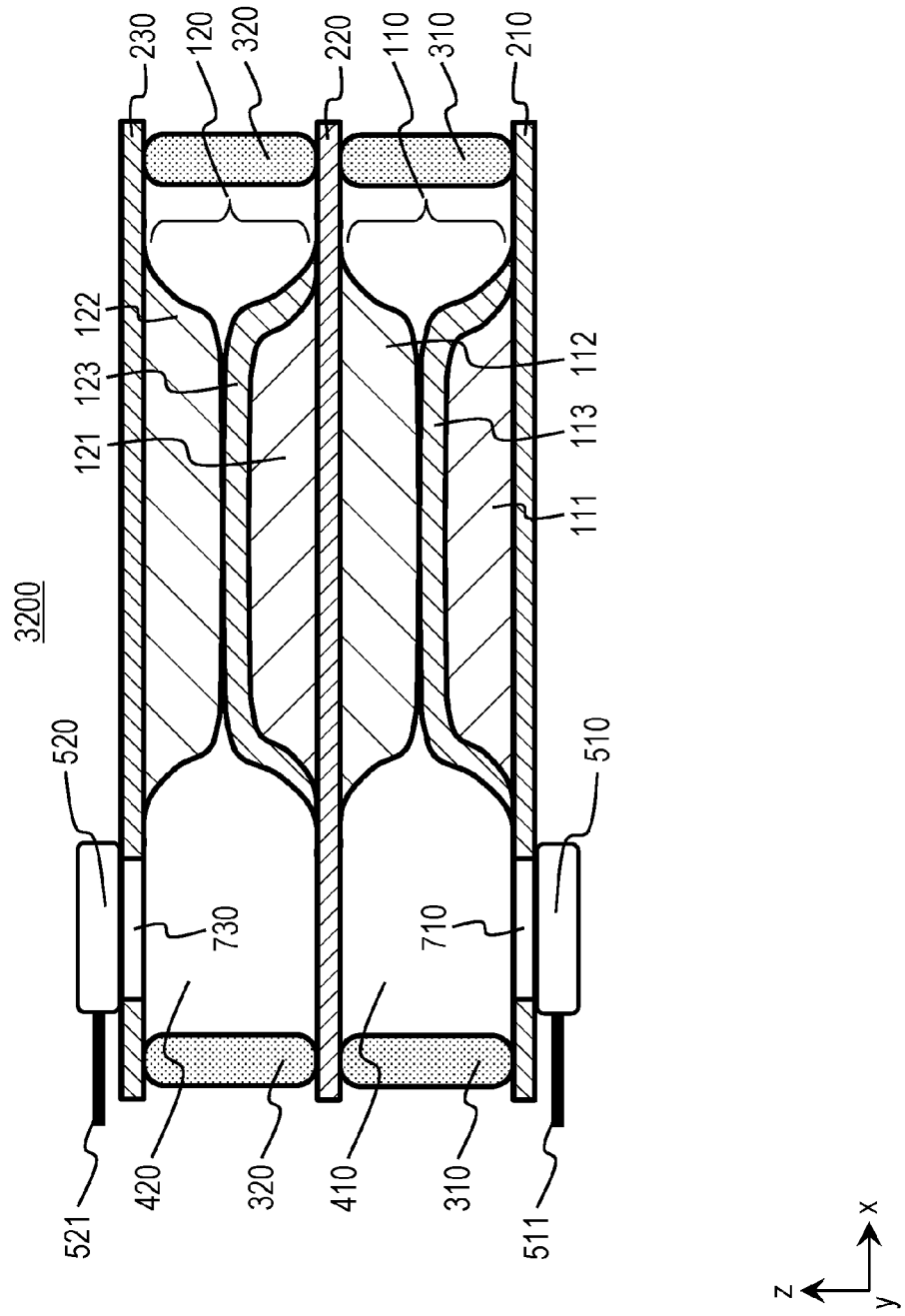
FIG. 15 is a schematic sectional view illustrating the structure of a battery according to the third embodiment.

FIG. 15 is a schematic sectional view illustrating the structure of a battery 3200 according to the third embodiment.

In the battery 3200 according to the third embodiment, the third current collector 230 has a third communication hole 730.

One end of the third communication hole 730 is connected to a second void 420.

The second gas detection unit 520 covers the other end of the third communication hole 730.

According to the above-described structure, the second gas detection unit 520 can be disposed outside the second void 420 (for example, on a side of the third current collector 230 opposite to the side that is in contact with the second counter electrode layer 122). The gas in the second void 420 can be introduced into the second gas detection unit 520 disposed outside the second void 420 through the third communication hole 730. Even when the second gas detection unit 520 cannot be disposed inside the second void 420, the gas in the second void 420 can be detected by the second gas detection unit 520 disposed outside the second void 420.

In addition, according to the above-described structure, the process of arranging (enclosing) the second gas detection unit 520 in the second void 420 can be omitted. Also, a process of forming an additional structure, such as a second sensor chamber 820 described below, can be omitted. Therefore, the manufacturing process of the battery can be simplified.

In the battery 3200 according to the third embodiment, as illustrated in FIG. 15, the third communication hole 730 may be an opening smaller than the sensing region of the second gas detection unit 520.

Alternatively, the third communication hole 730 may instead be an opening larger than the sensing region of the second gas detection unit 520. In this case, the gap between the sensing region of the second gas detection unit 520 and the third communication hole 730 may be sealed with a sealing member or the like.

A member for reinforcing the connection between the second gas detection unit 520 and the third current collector 230 may be used when the second gas detection unit 520 covers one end of the third communication hole 730. In this case, the second gas detection unit 520 can be prevented from being separated (for example, peeled off) from the third current collector 230.

The member for reinforcing the connection between the second gas detection unit 520 and the third current collector 230 may be, for example, an adhesive. More specifically, the second gas detection unit 520 and the third current collector 230 may be bonded together by applying an adhesive to the contact portions of the second gas detection unit 520 and the third current collector 230.

Alternatively, the member for reinforcing the connection between the second gas detection unit 520 and the third current collector 230 may be, for example, a structure such as the second sensor chamber 820 described below.

Figure 16:
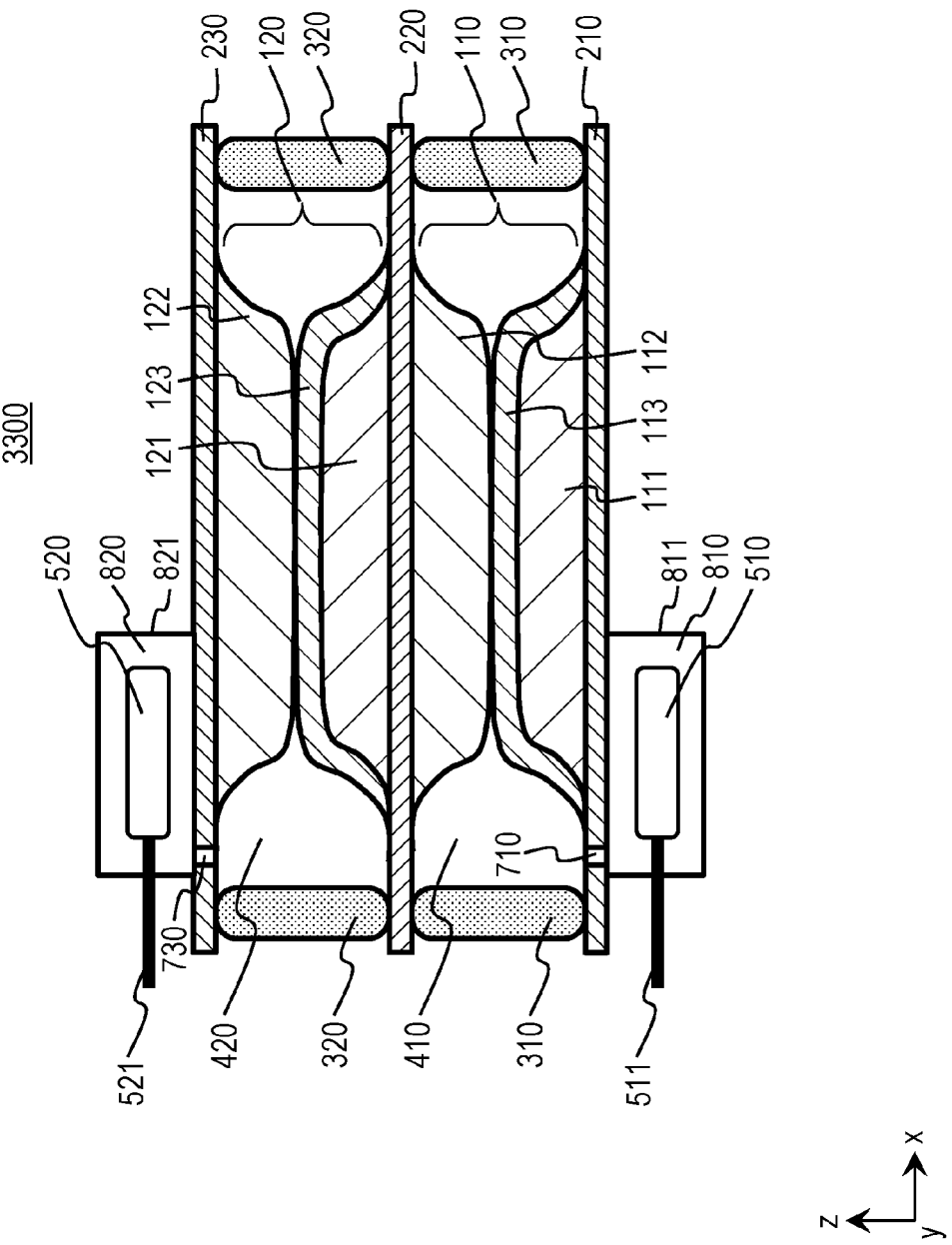
FIG. 16 is a schematic sectional view illustrating the structure of a battery according to the third embodiment.

FIG. 16 is a schematic sectional view illustrating the structure of a battery 3300 according to the third embodiment.

The battery 3300 according to the third embodiment further includes a second sensor chamber 820.

The second gas detection unit 520 is disposed in the second sensor chamber 820.

The third current collector 230 has a third communication hole 730.

The second void 420 is connected to the second sensor chamber 820 through the third communication hole 730.

According to the above-described structure, the second gas detection unit 520 can be disposed outside the second void 420 (for example, on a side of the third current collector 230 opposite to the side that is in contact with the second counter electrode layer 122). The gas in the second void 420 can be introduced into the second gas detection unit 520 disposed outside the second void 420 through the third communication hole 730. Even when the second gas detection unit 520 cannot be disposed inside the second void 420, the gas in the second void 420 can be detected by the second gas detection unit 520 disposed outside the second void 420.

In addition, according to the above-described structure, the process of arranging (enclosing) the second gas detection unit 520 in the second void 420 can be omitted. Therefore, the manufacturing process of the battery can be simplified.

In the above-described structure, the size of the third communication hole 730 may be reduced within a range in which the gas can be introduced into the second sensor chamber 820. In other words, the size of the third communication hole 730 may be smaller than that in the case where the second gas detection unit 520 covers the third communication hole 730 (as in the above-described battery 3200). For example, the size of the third communication hole 730 may be smaller than the detection region of the second gas detection unit 520. Accordingly, in the third current collector 230, the area in which the third communication hole 730 is formed can be reduced. As a result, the size of the battery can be reduced.

As illustrated in FIG. 16, in the battery 3300 according to the third embodiment, the second sensor chamber 820 may be a space surrounded by a second sensor chamber wall 821.

The second sensor chamber wall 821 may be made of, for example, a commonly known material of an outer cover body of a battery.

In the battery 3300 according to the third embodiment, as illustrated in FIG. 16, the second sensor chamber 820 may be in contact with (and in parallel to) the third current collector 230. In this case, the principal surfaces of the second sensor chamber 820 may be smaller than the principal surfaces of the third current collector 230. Thus, the size of the space in which the gas is detected (that is, the second sensor chamber 820) can be reduced.

In the battery 3300 according to the third embodiment, as illustrated in FIG. 16, the size of the second sensor chamber 820 may be larger than the size of the sensing region of the second gas detection unit 520. More specifically, the sensing region of the second gas detection unit 520 may be surrounded by (for example, sealed by) the second sensor chamber wall 821. In this case, the second connection lines 521 connected to the second gas detection unit 520 may extend to the outside of the battery through the second sensor chamber wall 821.

In the case where the battery 3300 according to the third embodiment is accommodated in an outer cover body, the second sensor chamber 820 may be disposed inside the outer cover body. Alternatively, the second sensor chamber 820 may instead be disposed outside the outer cover body.

In the third embodiment, the third communication hole 730 may be a rectangular opening. Alternatively, the third communication hole 730 may be a circular opening. Alternatively, the third communication hole 730 may be a slit-shaped opening.

In the third embodiment, the third communication hole 730 may be formed as a single opening. Alternatively, the third communication hole 730 may be formed as a plurality of openings.

In the third embodiment, the second power generating element 120 may include a second solid electrolyte layer 123.

The second solid electrolyte layer 123 may be disposed between the second electrode layer 121 and the second counter electrode layer 122.

At least one of the second electrode layer 121, the second counter electrode layer 122, and the second solid electrolyte layer 123 may contain a second sulfur-based material.

The gas may contain hydrogen sulfide gas generated due to the second sulfur-based material.

The second gas detection unit 520 may detect "the hydrogen sulfide gas in the second void 420."

According to the above-described structure, a laminate battery (bipolar all-solid battery) including a solid electrolyte can be realized, and the hydrogen sulfide gas detection sensitivity can be increased.

Fourth Embodiment

A fourth embodiment will now be described. Description of structures that are the same as those in any one of the first to third embodiments will be omitted as appropriate.

Figure 17:
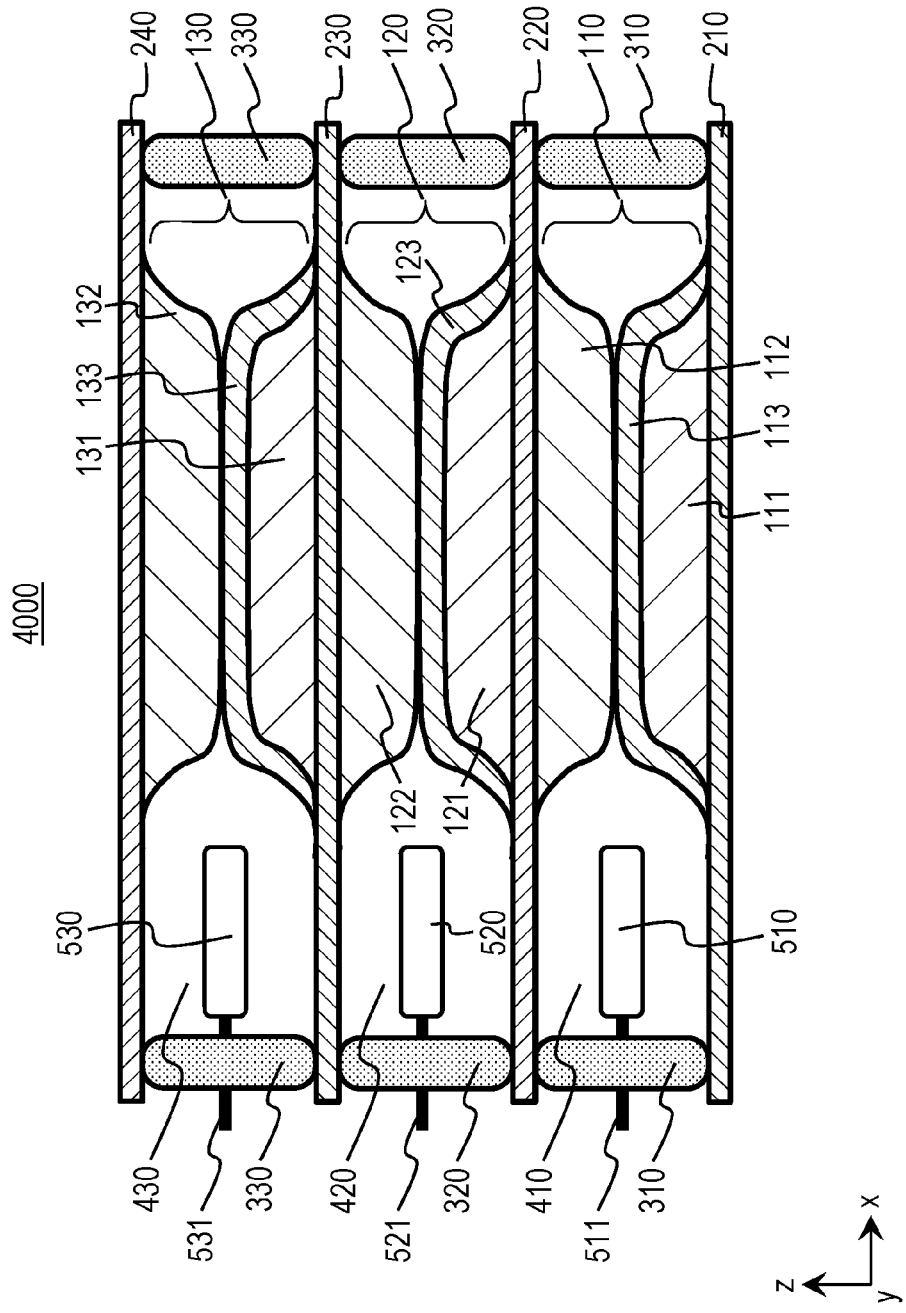
FIG. 17 is a schematic sectional view illustrating the structure of a battery according to a fourth embodiment.

FIG. 17 is a schematic sectional view illustrating the structure of a battery 4000 according to the fourth embodiment.

The battery 4000 according to the fourth embodiment includes the following structure in addition to the structure of the battery according to the third embodiment.

More specifically, the battery 4000 according to the fourth embodiment additionally includes a third power generating element 130, a fourth current collector 240, a third sealing portion 330, a third void 430, and a third gas detection unit 530.

The third power generating element 130 includes a third electrode layer 131 and a third counter electrode layer 132.

The third electrode layer 131 is in contact with the third current collector 230.

The third current collector 230 is electrically connected to the second current collector 220. The third current collector 230 may be electrically connected to the second current collector 220 through, for example, the second power generating element 120, as illustrated in FIG. 17.

The fourth current collector 240 is in contact with the third counter electrode layer 132.

The third sealing portion 330 seals the gap between the third current collector 230 and the fourth current collector 240.

The third void 430 is disposed between the third sealing portion 330 and the third power generating element 130.

The third gas detection unit 530 detects "gas in the third void 430."

According to the above-described structure, the gas generated in the first void 410 and the gas generated in the third void 430 can be accurately detected by the first gas detection unit 510 and the third gas detection unit 530, respectively.

According to the above-described structure, gas (for example, hydrogen sulfide gas) can be detected at high detection sensitivity. More specifically, the third sealing portion 330 limits the space accommodating the third power generating element 130, which may generate gas, to the third void 430, which is a small space. Thus, the third void 430, which is a small space, serves as a detection space in which the gas is detected. Accordingly, unlike the case in which the detection space is a larger space in the battery (for example, the space inside an outer cover body), the gas generated by the third power generating element 130 can be prevented from being dissipated and diluted in the larger space. The gas generated by the third power generating element 130 remains in a smaller space, that is, in the third void 430. Therefore, the third gas detection unit 530 can detect "the gas in the third void 430" at an early stage while the concentration of the gas is high. As a result, the gas detection sensitivity can be increased.

In addition, according to the above-described structure, the safety of the battery can be increased. More specifically, the regions around the first power generating element 110 and the third power generating element 130, which may generate gas, are surrounded (for example, sealed) by the first sealing portion 310 and the third sealing portion 330, respectively. When, for example, the battery further includes an outer cover body, the outer cover body, the first sealing portion 310, and the third sealing portion 330 form a multilayer safety structure. Accordingly, the gas generated by the first power generating element 110 and the gas generated by the third power generating element 130 are prevented from being immediately dissipated in the space inside the battery (for example, the space inside the outer cover body) or to the outside of the battery. Therefore, even if the sealed outer cover body is fractured or corroded when the gas is detected, the risk of leakage of harmful gas (for example, hydrogen sulfide gas) to the outside of the battery can be considerably reduced. Thus, the safety of the battery can be increased.

The structure, shape, and material of the above-described first gas detection unit 510 may be used as those of the third gas detection unit 530.

The structure, shape, and material of the third gas detection unit 530 may be the same as or different from those of the first gas detection unit 510 or the second gas detection unit 520.

In the battery 4000 according to the fourth embodiment, as illustrated in FIG. 17, the third gas detection unit 530 may be disposed in the third void 430.

According to the above-described structure, the gas detection sensitivity can be increased. More specifically, the gas generated by the third power generating element 130 and remaining in the third void 430 can be detected in the third void 430. Therefore, the third gas detection unit 530 can detect "the gas in the third void 430" at an early stage while the concentration of the gas is high.

Referring to FIG. 17, the battery 4000 according to the fourth embodiment may further include two third connection lines 531.

The third gas detection unit 530 may include a sensing region (for example, a portion formed of a resistance variable material) that is connected to one end of each of the two third connection lines 531.

In the battery 4000 according to the fourth embodiment, the other end of each of the two third connection lines 531 extends to, for example, the outside of the battery 4000 through the third sealing portion 330.

The two third connection lines 531 that extend to the outside of the battery 4000 may be connected to a detection device for detecting gas. The detection device may or may not be the same device as the detection device to which the first connection lines 511 are connected (in other words, to which the first gas detection unit 510 is connected).

Figure 18:
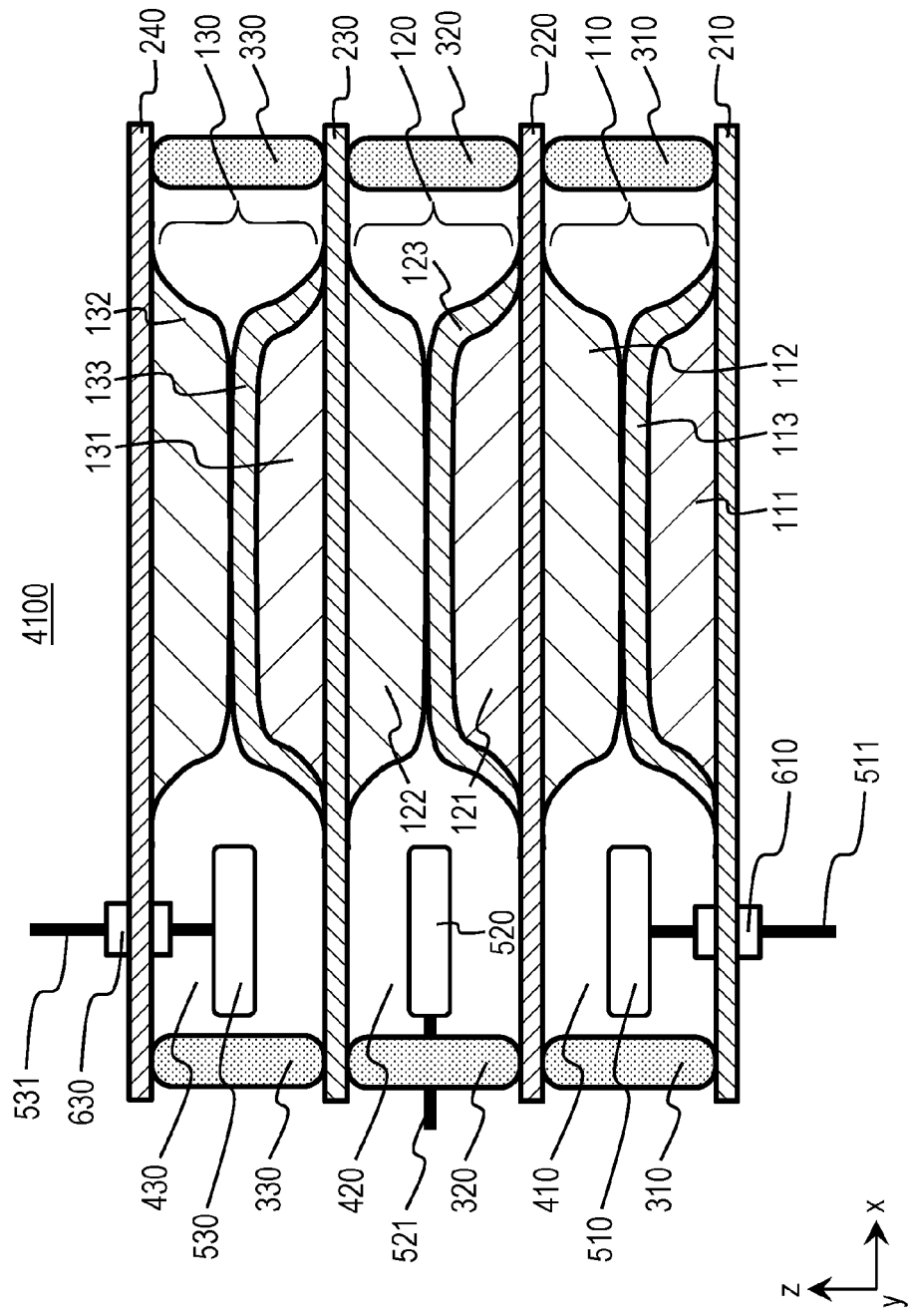
FIG. 18 is a schematic sectional view illustrating the structure of a battery according to the fourth embodiment.

FIG. 18 is a schematic sectional view illustrating the structure of a battery 4100 according to the fourth embodiment.

In the battery 4100 according to the fourth embodiment, the fourth current collector 240 includes third passage portions 630.

The third gas detection unit 530 includes third connection lines 531.

The third connection lines 531 extend to the outside through the third passage portions 630.

According to the above-described structure, the structure for enabling the third connection lines 531 of the third gas detection unit 530 to extend to the outside can be more easily formed than in the case where the third connection lines 531 extend to the outside through the third sealing portion 330 (as in the above-described battery 4000).

Each third passage portion 630 may include, for example, an opening formed in the fourth current collector 240 and a sealing portion that seals the gap between the opening and the corresponding third connection line 531. The material of the sealing portion may be the same as the material of the above-described first sealing portion 310.

Figure 19:
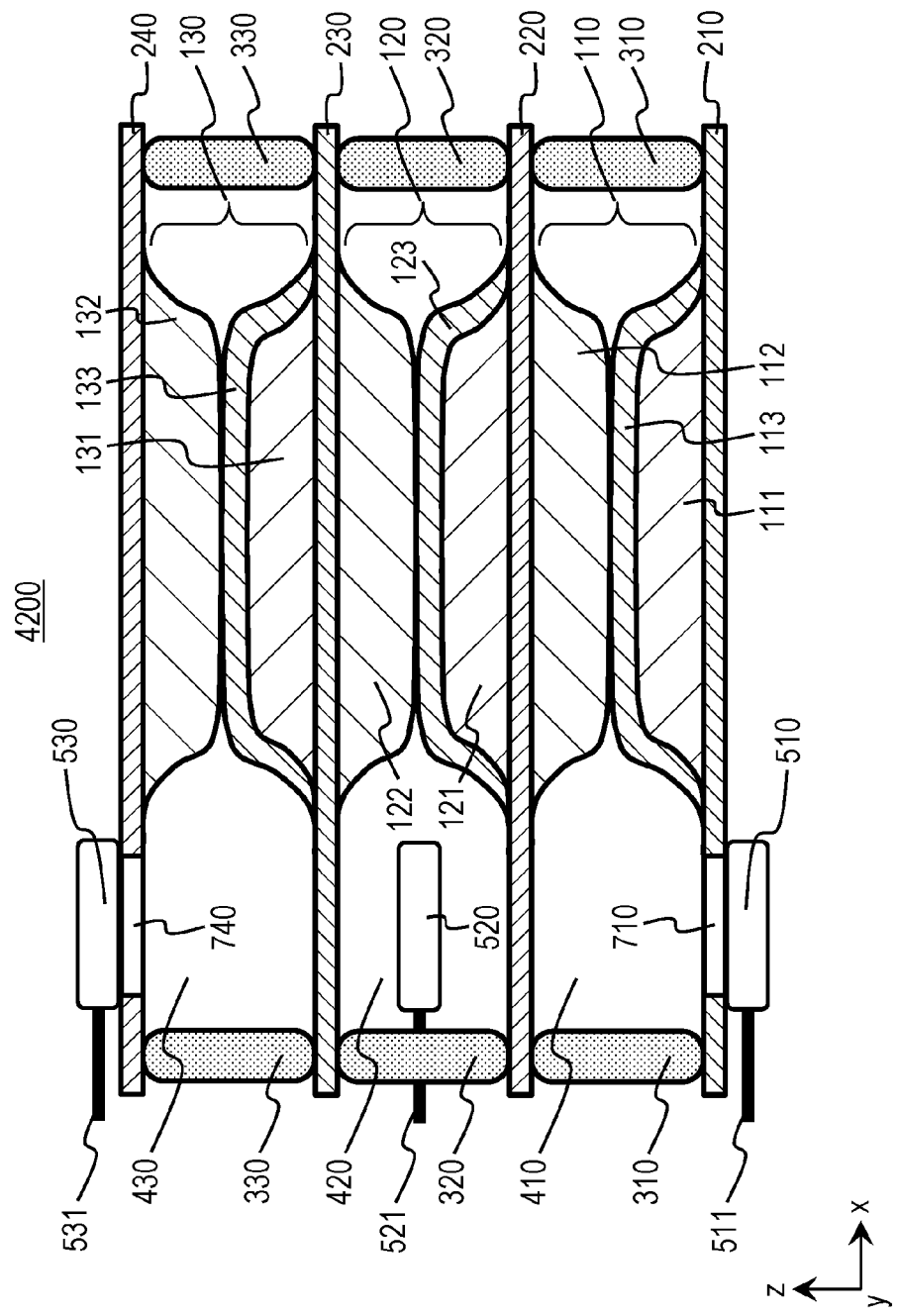
FIG. 19 is a schematic sectional view illustrating the structure of a battery according to the fourth embodiment.

FIG. 19 is a schematic sectional view illustrating the structure of a battery 4200 according to the fourth embodiment.

In the battery 4200 according to the fourth embodiment, the fourth current collector 240 has a fourth communication hole 740.

One end of the fourth communication hole 740 is connected to a third void 430.

The third gas detection unit 530 covers the other end of the fourth communication hole 740.

According to the above-described structure, the third gas detection unit 530 can be disposed outside the third void 430 (for example, on a side of the fourth current collector 240 opposite to the side that is in contact with the third counter electrode layer 132). The gas in the third void 430 can be introduced into the third gas detection unit 530 disposed outside the third void 430 through the fourth communication hole 740. Even when the third gas detection unit 530 cannot be disposed inside the third void 430, the gas in the third void 430 can be detected by the third gas detection unit 530 disposed outside the third void 430.

In addition, according to the above-described structure, the process of arranging (enclosing) the third gas detection unit 530 in the third void 430 can be omitted. Also, a process of forming an additional structure, such as a third sensor chamber 830 described below, can be omitted. Therefore, the manufacturing process of the battery can be simplified.

In the battery 4200 according to the fourth embodiment, as illustrated in FIG. 19, the fourth communication hole 740 may be an opening smaller than the sensing region of the third gas detection unit 530.

Alternatively, the fourth communication hole 740 may instead be an opening larger than the sensing region of the third gas detection unit 530. In this case, the gap between the sensing region of the third gas detection unit 530 and the fourth communication hole 740 may be sealed with a sealing member or the like.

A member for reinforcing the connection between the third gas detection unit 530 and the fourth current collector 240 may be used when the third gas detection unit 530 covers one end of the fourth communication hole 740. In this case, the third gas detection unit 530 can be prevented from being separated (for example, peeled off) from the fourth current collector 240.

The member for reinforcing the connection between the third gas detection unit 530 and the fourth current collector 240 may be, for example, an adhesive. More specifically, the third gas detection unit 530 and the fourth current collector 240 may be bonded together by applying an adhesive to the contact portions of the third gas detection unit 530 and the fourth current collector 240.

Alternatively, the member for reinforcing the connection between the third gas detection unit 530 and the fourth current collector 240 may be, for example, a structure such as the third sensor chamber 830 described below.

Figure 20:
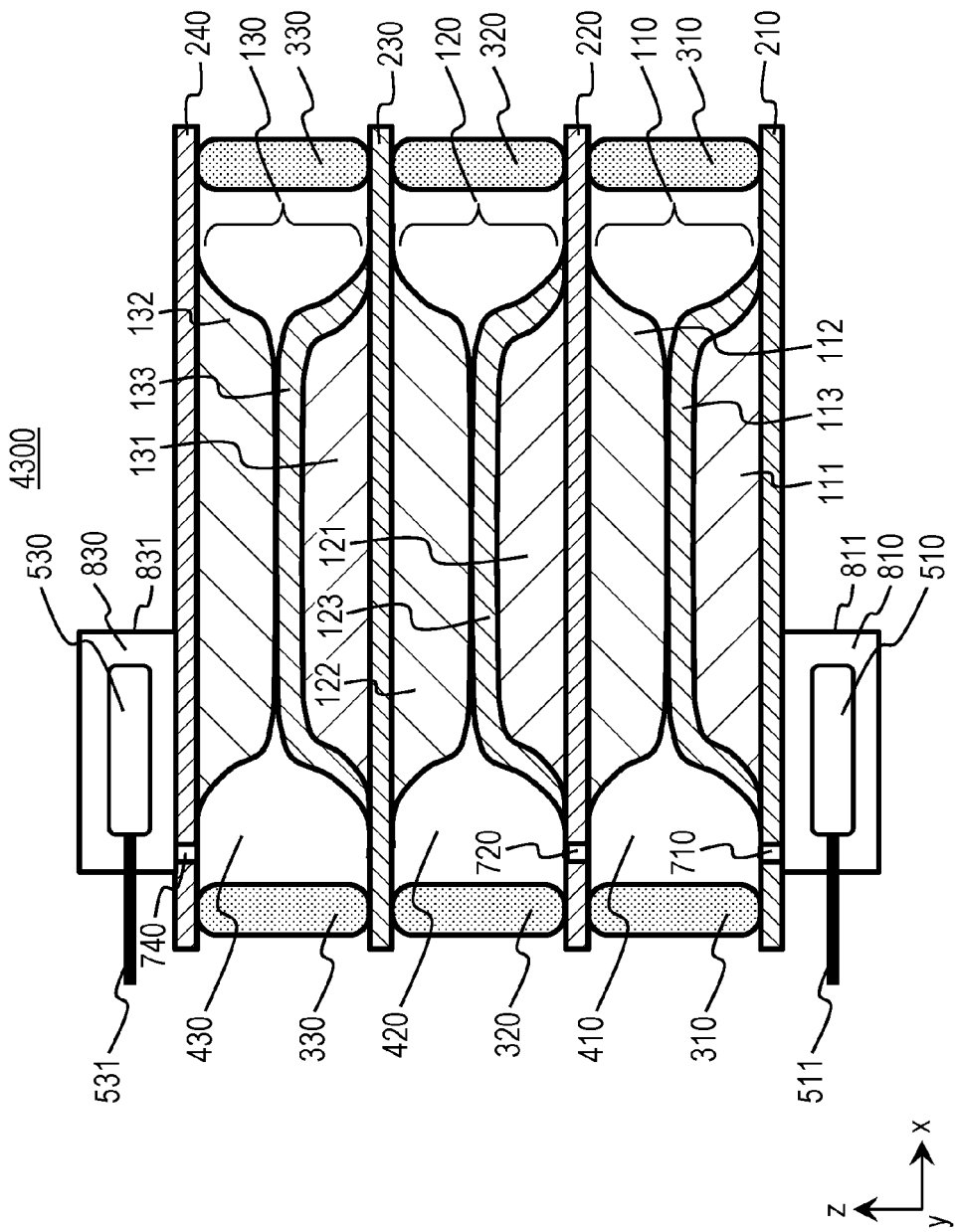
FIG. 20 is a schematic sectional view illustrating the structure of a battery according to the fourth embodiment.

FIG. 20 is a schematic sectional view illustrating the structure of a battery 4300 according to the fourth embodiment.

The battery 4300 according to the fourth embodiment further includes a third sensor chamber 830.

The third gas detection unit 530 is disposed in the third sensor chamber 830.

The fourth current collector 240 has a fourth communication hole 740.

The third void 430 is connected to the third sensor chamber 830 through the fourth communication hole 740.

According to the above-described structure, the third gas detection unit 530 can be disposed outside the third void 430 (for example, on a side of the fourth current collector 240 opposite to the side that is in contact with the third counter electrode layer 132). The gas in the third void 430 can be introduced into the third gas detection unit 530 disposed outside the third void 430 through the fourth communication hole 740. Even when the third gas detection unit 530 cannot be disposed inside the third void 430, the gas in the third void 430 can be detected by the third gas detection unit 530 disposed outside the third void 430.

In addition, according to the above-described structure, the process of arranging (enclosing) the third gas detection unit 530 in the third void 430 can be omitted. Therefore, the manufacturing process of the battery can be simplified.

In the above-described structure, the size of the fourth communication hole 740 may be reduced within a range in which the gas can be introduced into the third sensor chamber 830. In other words, the size of the fourth communication hole 740 may be smaller than that in the case where the third gas detection unit 530 covers the fourth communication hole 740. For example, the size of the fourth communication hole 740 may be smaller than the detection region of the third gas detection unit 530. Accordingly, in the fourth current collector 240, the area in which the fourth communication hole 740 is formed can be reduced. As a result, the size of the battery can be reduced.

As illustrated in FIG. 20, in the battery 4300 according to the fourth embodiment, the third sensor chamber 830 may be a space surrounded by a third sensor chamber wall 831.

The third sensor chamber wall 831 may be made of, for example, a commonly known material of an outer cover body of a battery.

In the battery 4300 according to the fourth embodiment, as illustrated in FIG. 20, the third sensor chamber 830 may be in contact with (and in parallel to) the fourth current collector 240. In this case, the principal surface of the third sensor chamber 830 may be smaller than the principal surfaces of the fourth current collector 240. Thus, the size of the space in which the gas is detected (that is, the third sensor chamber 830) can be reduced.

In the battery 4300 according to the fourth embodiment, as illustrated in FIG. 20, the size of the third sensor chamber 830 may be larger than the size of the sensing region of the third gas detection unit 530. More specifically, the sensing region of the third gas detection unit 530 may be surrounded by (for example, sealed by) the third sensor chamber wall 831. In this case, the third connection lines 531 connected to the third gas detection unit 530 may extend to the outside of the battery through the third sensor chamber wall 831.

In the case where the battery 4300 according to the fourth embodiment is accommodated in an outer cover body, the third sensor chamber 830 may be disposed inside the outer cover body. Alternatively, the third sensor chamber 830 may instead be disposed outside the outer cover body.

In the fourth embodiment, the fourth communication hole 740 may be a rectangular opening. Alternatively, the fourth communication hole 740 may be a circular opening. Alternatively, the fourth communication hole 740 may be a slit-shaped opening.

In the fourth embodiment, the fourth communication hole 740 may be formed as a single opening. Alternatively, the fourth communication hole 740 may be formed as a plurality of openings.

In the battery 4300 according to the fourth embodiment, as illustrated in FIG. 20, the gas generated in the second void 420 is introduced into the first gas detection unit 510, which is disposed at the bottom of the battery 4300, through the second communication hole 720 formed in the second current collector 220.

According to the above-described structure, even when a lower section of the battery 4300 is filled with gas (for example, hydrogen sulfide gas that is heavier than atmospheric air) that is generated when external gas (for example, atmospheric air) enters the battery 4300, the gas that fills the lower section of the battery 4300 can be detected by the first gas detection unit 510 disposed at the bottom of the battery 4300. Therefore, the first gas detection unit 510 can detect the gas generated in the second void 420 at an early stage while the concentration of the gas is high. As a result, the gas detection sensitivity can be increased.

Figure 21:
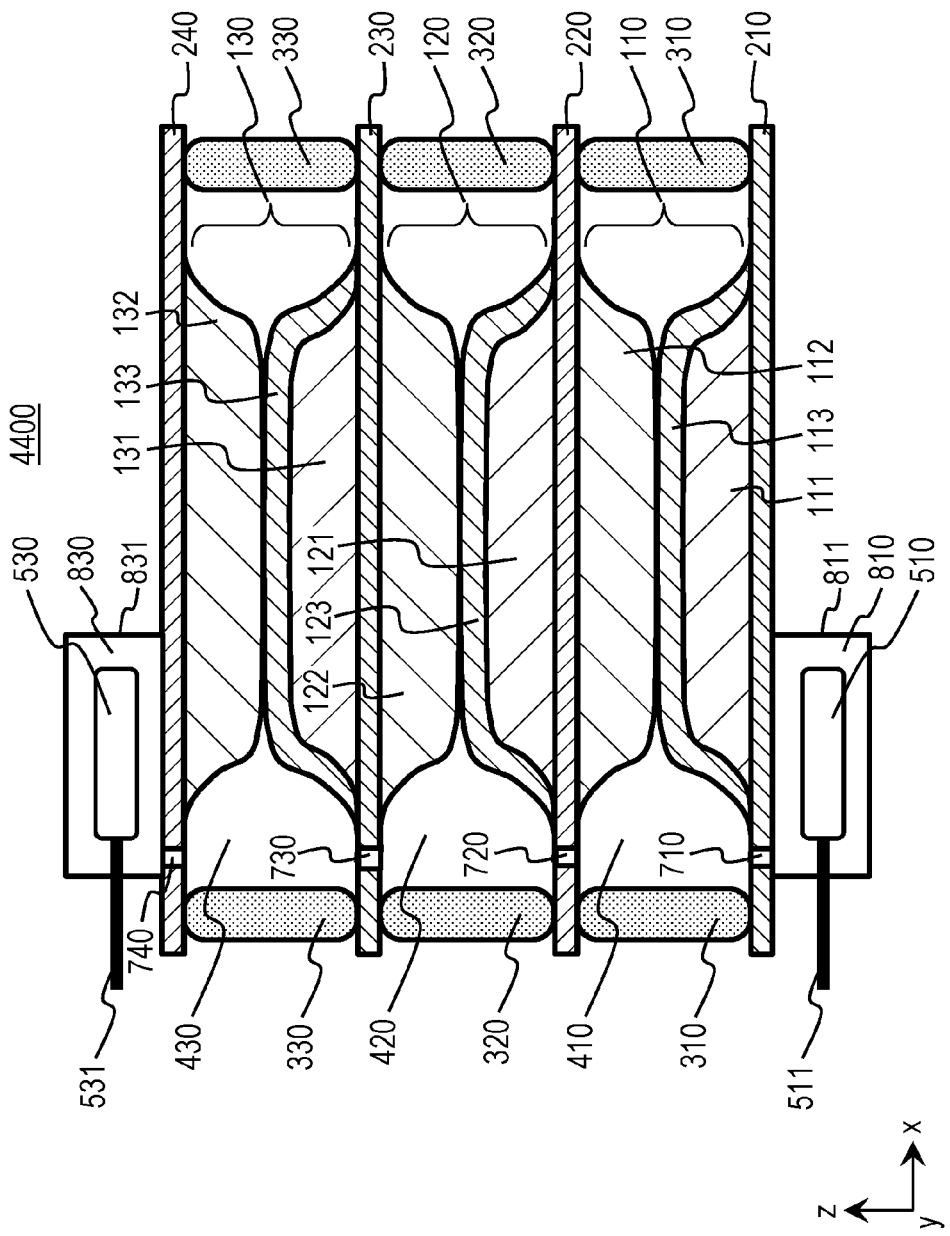
FIG. 21 is a schematic sectional view illustrating the structure of a battery according to the fourth embodiment.

FIG. 21 is a schematic sectional view illustrating the structure of a battery 4400 according to the fourth embodiment.

In the battery 4400 according to the fourth embodiment, the first void 410 and the third void 430 are connected to each other.

According to the above-described structure, the gas generated in the first void 410, the gas generated in the second void 420, and the gas generated in the third void 430 can be detected by both the first gas detection unit 510 and the third gas detection unit 530. When, for example, a lower section of the battery 4400 is filled with gas (for example, hydrogen sulfide gas that is heavier than atmospheric air) that is generated when external gas (for example, atmospheric air) enters the battery 4400, the gas that fills the lower section of the battery 4400 can be detected by the first gas detection unit 510 disposed at the bottom of the battery 4400. When, for example, an upper section of the battery 4400 is filled with gas (for example, gas that is lighter than atmospheric air) that is generated when external gas (for example, atmospheric air) enters the battery 4400, the gas that fills the upper section of the battery 4400 can be detected by the third gas detection unit 530 disposed at the top of the battery 4400. As a result, the gas detection sensitivity can be increased.

As illustrated in FIG. 21, the first void 410 and the third void 430 may be connected to each other through, for example, the second communication hole 720, the second void 420, and the third communication hole 730.

Figure 22:
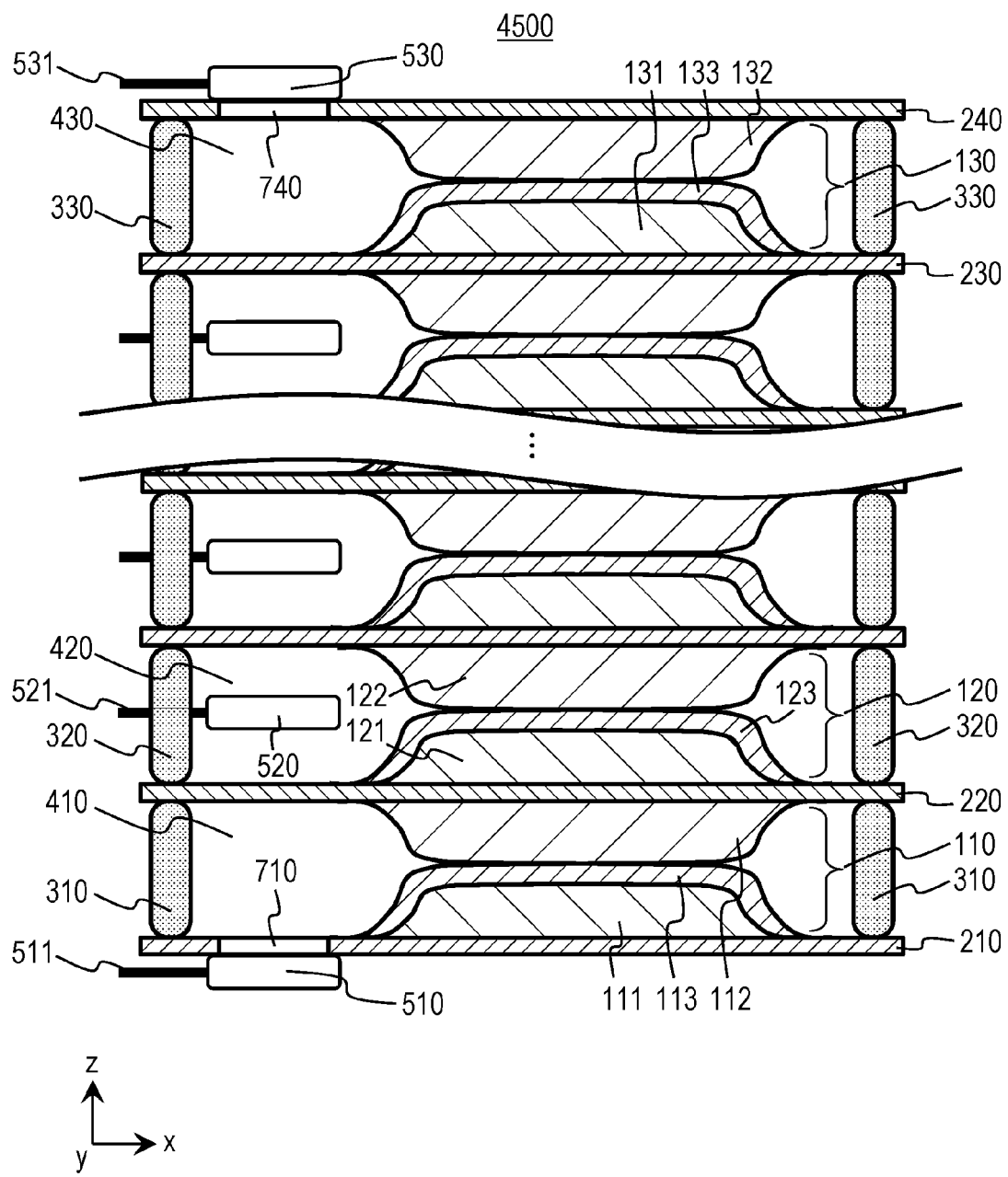
FIG. 22 is a schematic sectional view illustrating the structure of a battery according to the fourth embodiment.

FIG. 22 is a schematic sectional view illustrating the structure of a battery 4500 according to the fourth embodiment.

In the fourth embodiment, as illustrated in FIG. 22, the battery may be formed by stacking four or more power generating elements.

In the battery 4500 illustrated in FIG. 22, a plurality of power generating elements and a plurality of current collectors are stacked between the second power generating element 120 and the third current collector 230.

In the battery 4500 illustrated in FIG. 22, the third current collector 230 is electrically connected to the second current collector 220 through the power generating elements and the current collectors disposed between the second power generating element 120 and the third current collector 230 and the second power generating element 120.

In addition, in the battery 4500 illustrated in FIG. 22, each of the power generating elements is sealed by a sealing portion at the periphery thereof. Accordingly, a void is formed between each of the power generating elements and the sealing portion.

In addition, in the battery 4500 illustrated in FIG. 22, a plurality of detection sensors that correspond to the voids are provided.

Each of the current collectors disposed between the second power generating element 120 and the third current collector 230 may have a communication hole. In such a case, the voids between the power generating elements and the sealing portions are connected to each other.

In the fourth embodiment, the third power generating element 130 may include a third solid electrolyte layer 133.

The third solid electrolyte layer 133 may be disposed between the third electrode layer 131 and the third counter electrode layer 132.

At least one of the third electrode layer 131, the third counter electrode layer 132, and the third solid electrolyte layer 133 may contain a third sulfur-based material.

The gas may contain hydrogen sulfide gas generated due to the third sulfur-based material.

The third gas detection unit 530 may detect the hydrogen sulfide gas in the third void 430.

According to the above-described structure, a laminate battery (bipolar all-solid battery) including a solid electrolyte can be realized, and the hydrogen sulfide gas detection sensitivity can be increased.

Fifth Embodiment

A fifth embodiment will now be described. Description of structures that are the same as those in any one of the first to fourth embodiments will be omitted as appropriate.

Figure 23:
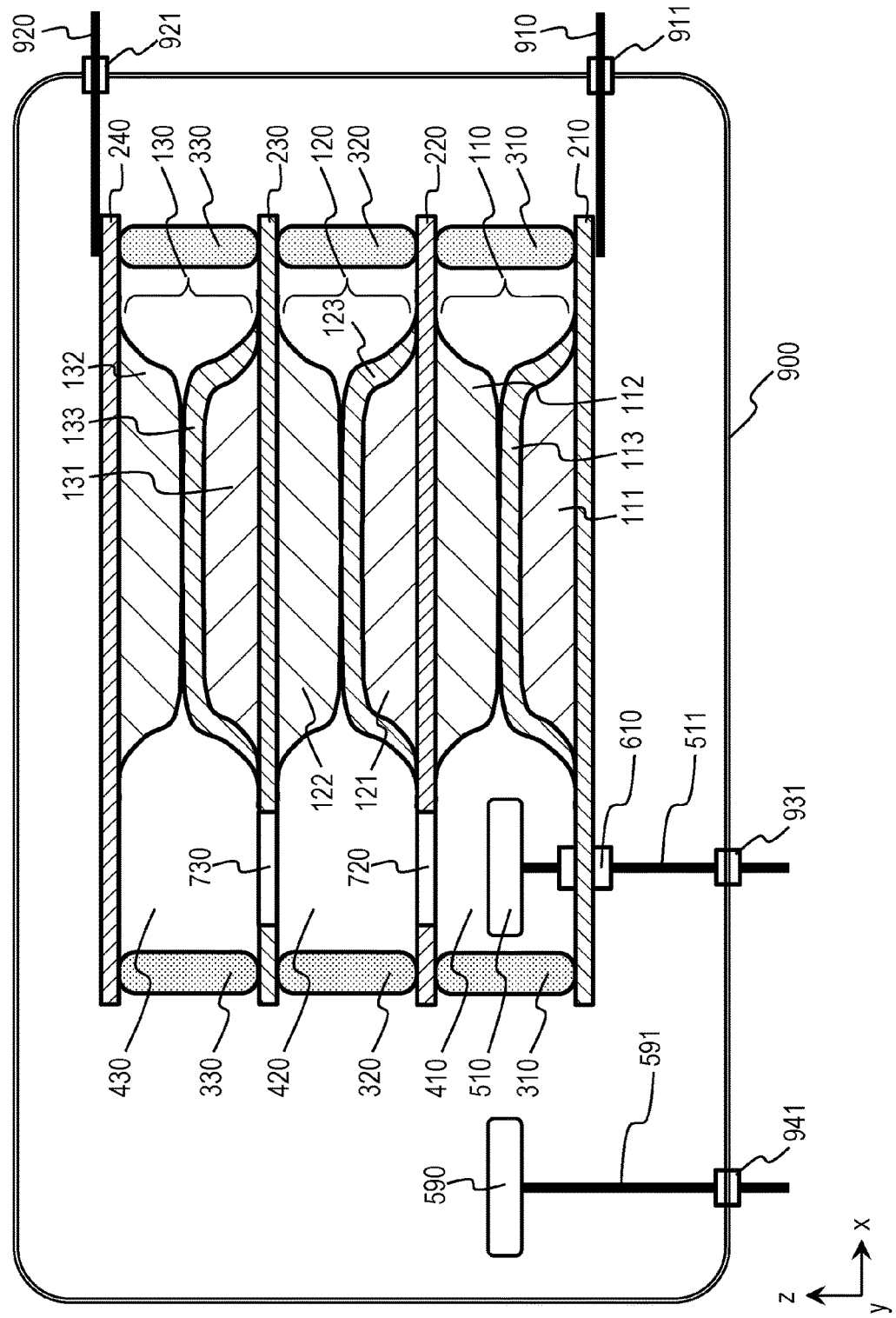
FIG. 23 is a schematic sectional view illustrating the structure of a battery according to a fifth embodiment.

FIG. 23 is a schematic sectional view illustrating the structure of a battery 5000 according to the fifth embodiment.

The battery 5000 according to the fifth embodiment includes the following structure in addition to the structure of the battery according to the first to fourth embodiments.

More specifically, the battery 5000 according to the fifth embodiment additionally includes an outer cover body 900 and an outer gas detection unit 590.

The outer cover body 900 accommodates (for example, seals) the first power generating element 110.

The outer gas detection unit 590 detects gas.

The outer gas detection unit 590 is located outside the space surrounded by the first sealing portion 310, the first current collector 210, and the second current collector 220, and inside the outer cover body 900.

According to the above-described structure, when, for example, the outer cover body 900 is damaged, components of gas that flows into the outer cover body 900 from the outside can be detected by the outer gas detection unit 590. In addition, gas generated by the power generating elements can also be detected by the outer gas detection unit 590.

In the fifth embodiment, as illustrated in FIG. 23, the outer cover body 900 may accommodate (for example, seal) the first power generating element 110, the second power generating element 120, and the third power generating element 130. In other words, the outer cover body 900 may accommodate (for example, seal) the battery according to any one of the above-described first to fourth embodiments.

In the fifth embodiment, as illustrated in FIG. 23, the outer gas detection unit 590 may be located outside the space surrounded by the first current collector 210, the fourth current collector 240, and the sealing portions, and inside the outer cover body 900. In other words, the outer gas detection unit 590 may be located outside the battery according to any one of the above-described first to fourth embodiments and inside the outer cover body 900.

The outer cover body 900 may be made of a commonly known outer cover material (for example, an aluminum foil, an aluminum alloy foil, a resin film, or a composite film made of aluminum and a resin). The material of the outer cover body 900 may have a high ability to prevent permeation of, for example, water, enclosed gas, or gas that may be generated by the power generating elements. The outer cover body 900 prevents entrance of water, thereby preventing, for example, corrosion and deterioration of the current collectors, degeneration of the solid electrolyte, and generation of toxic gas.

The structure, shape, and material of the above-described first gas detection unit 510 may be used as those of the outer gas detection unit 590.

The structure, shape, and material of the outer gas detection unit 590 may be the same as or different from those of the first gas detection unit 510.

The battery 5000 according to the fifth embodiment may further include connection lines 591.

The outer gas detection unit 590 may include a sensing region (for example, a portion formed of a resistance variable material) that is connected to one end of each connection line 591.

In the battery 5000 according to the fifth embodiment, the other end of each connection line 591 extends to, for example, the outside of the battery 5000 through the outer cover body 900. The gap between each connection line 591 and the outer cover body 900 may be sealed by, for example, a sealing portion 941.

The connection lines 591 that extend to the outside of the battery 5000 may be connected to a detection device for detecting gas. The detection device may or may not be the same device as the detection device to which the first connection lines 511 are connected (in other words, to which the first gas detection unit 510 is connected).

The batteries according to the above-described first to fourth embodiments may also include the outer cover body 900 as in the fifth embodiment.

In such a case, each of the batteries according to the first to fifth embodiments may further include a first lead wire 910 and a second lead wire 920.

One end of the first lead wire 910 is connected to the first current collector 210. The other end of the first lead wire 910 extends to the outside of the outer cover body 900. The gap between the first lead wire 910 and the outer cover body 900 may be sealed by, for example, a sealing portion 911.

One end of the second lead wire 920 is connected to the current collector that serves as a counter electrode for the first current collector 210 (for example, the fourth current collector 240 in the example illustrated in FIG. 23). The other end of the second lead wire 920 extends to the outside of the outer cover body 900. The gap between the second lead wire 920 and the outer cover body 900 may be sealed by, for example, a sealing portion 921.

The first lead wire 910 and the second lead wire 920 may be connected to a load to which the battery according to any one of the first to fifth embodiments supplies electric power, or a charging device that charges the battery according to any one of the first to fifth embodiments.

In the battery according to any one of the first to fifth embodiments, the first connection lines 511 connected to the sensing region of the first gas detection unit 510 may extend to the outside of the outer cover body 900. In this case, the gap between each first connection line 511 and the outer cover body 900 may be sealed by, for example, a sealing portion 931. In the case where a plurality of gas detection units are provided, the connection lines connected to each of the gas detection units may extend to the outside of the outer cover body 900 in a similar manner.

The structures according to the above-described first to fifth embodiments may be applied in combination.

The battery according to the present disclosure may be used as, for example, an all-solid lithium secondary battery.

What is claimed is:

1. A battery comprising:
a first power generator including a first electrode layer and a first counter electrode layer;
a first current collector that is in contact with the first electrode layer;
a second current collector that is in contact with the first counter electrode layer;
a first seal that seals a first gap and that is entirely between the first current collector and the second current collector;
a first void disposed between the first seal and the first power generator; and
a first gas detector that detects a first gas type,
wherein the first gas detector detects the first gas type in the first void.

2. The battery according to claim 1,
wherein the first gas type is a first gas component.

3. The battery according to claim 1,
wherein the first current collector includes a first communication hole,
wherein one end of the first communication hole is connected to the first void, and
wherein the first gas detector covers an other end of the first communication hole.

4. The battery according to claim 1, further comprising:
a first sensor chamber,
wherein the first gas detector is disposed in the first sensor chamber, and
wherein the first current collector has a first communication hole that connects the first void to the first sensor chamber.

5. The battery according to claim 1, further comprising:
an outer cover body that accommodates the first power generator; and
an outer gas detection unit that detects the first gas type,
wherein the outer gas detection unit is located outside a space surrounded by the first seal, the first current collector, and the second current collector and inside the outer cover body.

6. The battery according to claim 1,
wherein the first power generator includes a first solid electrolyte layer,
wherein the first solid electrolyte layer is disposed between the first electrode layer and the first counter electrode layer,
wherein at least one of the first electrode layer, the first counter electrode layer, and the first solid electrolyte layer includes a first sulfur-based material,
wherein the first gas type contains hydrogen sulfide gas generated due to the first sulfur-based material, and
wherein the first gas detector detects the hydrogen sulfide gas in the first void.

7. The battery according to claim 1,
wherein the first gas detector is disposed in the first void.

8. The battery according to claim 7,
wherein the first current collector includes a first passage,
wherein the first gas detector includes a first connection line, and
wherein the first connection line extends to outside through the first passage.

9. The battery according to claim 1, further comprising:
a second power generator including a second electrode layer and a second counter electrode layer, the second electrode layer being in contact with the second current collector;
a third current collector that is in contact with the second counter electrode layer;
a second seal that seals a second gap between the second current collector and the third current collector; and
a second void disposed between the second seal and the second power generator,
wherein the second current collector includes a second communication hole that connects the first void to the second void.

10. The battery according to claim 9, further comprising:
a third power generator including a third electrode layer and a third counter electrode layer, the third electrode layer being in contact with the third current collector;
a fourth current collector that is in contact with the third counter electrode layer;
a third seal that seals a third gap between the third current collector and the fourth current collector; and
a third void disposed between the third seal and the third power generator,
wherein the third current collector includes a third communication hole that connects the second void to the third void.

11. The battery according to claim 1, further comprising:
a second power generator including a second electrode layer and a second counter electrode layer, the second electrode layer being in contact with the second current collector;
a third current collector that is in contact with the second counter electrode layer;
a second seal that seals a second gap between the second current collector and the third current collector;
a second void disposed between the second seal and the second power generator; and
a second gas detector that detects a second gas type,
wherein the second gas detector detects the second gas type in the second void.

12. The battery according to claim 11,
wherein the second gas type is a second gas component.

13. The battery according to claim 11,
wherein the third current collector includes a third communication hole,
wherein one end of the third communication hole is connected to the second void, and
wherein the second gas detector covers an other end of the third communication hole.

14. The battery according to claim 11, further comprising:
a second sensor chamber,
wherein the second gas detector is disposed in the second sensor chamber, and
wherein the third current collector has a third communication hole that connects the second void to the second sensor chamber.

15. The battery according to claim 11,
wherein the second power generator includes a second solid electrolyte layer,
wherein the second solid electrolyte layer is disposed between the second electrode layer and the second counter electrode layer,
wherein at least one of the second electrode layer, the second counter electrode layer, and the second solid electrolyte layer includes a second sulfur-based material, wherein the second gas type contains hydrogen sulfide gas generated due to the second sulfur-based material, and wherein the second gas detector detects the hydrogen sulfide gas in the second void.

16. The battery according to claim 11, wherein the second gas detector is disposed in the second void.

17. The battery according to claim 16, wherein the third current collector includes a second passage, wherein the second gas detector includes a second connection line, and wherein the second connection line extends to outside through the second passage.

18. The battery according to claim 1, further comprising:

a third power generator including a third electrode layer and a third counter electrode layer;

a third current collector that is electrically connected to the second current collector and in contact with the third electrode layer;

a fourth current collector that is in contact with the third counter electrode layer;

a third seal that seals a third gap between the third current collector and the fourth current collector;

a third void disposed between the third seal and the third power generator; and a third gas detector that detects a third gas type, wherein the third gas detector detects the third gas type in the third void.

19. The battery according to claim 18, wherein the fourth current collector includes a fourth communication hole, wherein one end of the fourth communication hole is connected to the third void, and wherein the third gas detection unit covers an other end of the fourth communication hole.

20. The battery according to claim 18, further comprising:

a third sensor chamber, wherein the third gas detection unit is disposed in the third sensor chamber, and wherein the fourth current collector has a fourth communication hole that connects the third void to the third sensor chamber.

21. The battery according to claim 18, wherein the third power generator includes a third solid electrolyte layer, wherein the third solid electrolyte layer is disposed between the third electrode layer and the third counter electrode layer, wherein at least one of the third electrode layer, the third counter electrode layer, and the third solid electrolyte layer includes a third sulfur-based material, wherein the third gas type contains hydrogen sulfide gas generated due to the third sulfur-based material, and wherein the third gas detection unit detects the hydrogen sulfide gas in the third void.

22. The battery according to claim 18, wherein the third gas detector is disposed in the third void.

23. The battery according to claim 22, wherein the fourth current collector includes a third passage, wherein the third gas detector includes a third connection line, and wherein the third connection line extends to outside through the third passage.

* * * * *